(12) United States Patent
Jackson et al.

(10) Patent No.: US 6,197,785 B1
(45) Date of Patent: Mar. 6, 2001

(54) ALKOXY-SUBSTITUTED COMPOUNDS, METHODS, AND COMPOSITIONS FOR INHIBITING PARP ACTIVITY

(75) Inventors: Paul F. Jackson, Bel Air; Keith M. Maclin, Baltimore; Jie Zhang, Ellicott City, all of MD (US)

(73) Assignee: Guilford Pharmaceuticals Inc., Baltimore, MD (US)

( * ) Notice: Subject to any disclaimer, the term of this patent is extended or adjusted under 35 U.S.C. 154(b) by 0 days.

(21) Appl. No.: 09/145,166

(22) Filed: Sep. 1, 1998

Related U.S. Application Data

(63) Continuation-in-part of application No. 09/079,508, filed on May 15, 1998, and application No. 08/922,520, filed on Sep. 3, 1997, now abandoned.

(51) Int. Cl.[7] .......................... C07D 217/24; A61K 31/47

(52) U.S. Cl. .......................... 514/309; 514/233.5; 514/299; 544/128; 546/141; 546/183

(58) Field of Search ............... 514/309, 233.5; 546/141, 183; 544/128

(56) References Cited

U.S. PATENT DOCUMENTS

| Re. 31,617 | 6/1984 | Beverung, Jr. et al. | 514/311 |
|---|---|---|---|
| 1,895,105 | 1/1933 | Rath et al. | 514/311 |
| 2,467,692 | 4/1949 | Petrow | 514/311 |
| 2,612,503 | 9/1952 | Ullyot | 514/310 |
| 3,300,499 | 1/1967 | Lesher | 514/311 |
| 3,557,119 | 1/1971 | Humber | 514/311 |
| 3,573,304 | 3/1971 | Eberle et al. | 260/250 |
| 3,700,673 | 10/1972 | Watson | 514/311 |
| 3,900,477 | 8/1975 | Philipp et al. | 514/311 |
| 3,950,343 | 4/1976 | Philipp et al. | . |
| 3,978,066 | 8/1976 | Philipp et al. | 514/311 |
| 3,991,064 | 11/1976 | Brown et al. | 514/311 |
| 4,031,097 | 6/1977 | Bach et al. | 514/311 |
| 4,472,401 | 9/1984 | Kennewell et al. | 514/511 |
| 4,742,171 | 5/1988 | Martin et al. | 514/311 |
| 4,902,695 | 2/1990 | Ornstein | 514/307 |
| 5,041,653 | 8/1991 | Lee et al. | 564/74 |
| 5,177,075 | 1/1993 | Suto et al. | 514/248 |
| 5,338,851 | 8/1994 | Huff et al. | 546/141 |
| 5,414,001 | 5/1995 | Ireland et al. | 514/311 |
| 5,420,136 | 5/1995 | Lewis et al. | 514/311 |
| 5,589,483 | 12/1996 | West | 514/310 |
| 5,618,813 | 4/1997 | Chu et al. | 514/311 |
| 5,756,510 | 5/1998 | Griffin et al. | 514/311 |
| 5,767,135 | 6/1998 | Fernandez-Pol | 514/354 |

FOREIGN PATENT DOCUMENTS

| 628 255 | 5/1963 | (BE) . |
| 601 246 | 6/1978 | (CH) . |
| 963 184 | 5/1957 | (DE) . |
| 0 355 750 | 2/1990 | (EP) . |
| 0 539 805 | 5/1993 | (EP) . |
| 2 305 182 | 10/1976 | (FR) . |
| 810 108 | 3/1959 | (GB) . |
| 1 474 775 | 5/1977 | (GB) . |
| WO 95/24379 | 9/1995 | (WO) . |
| WO 95/29895 | 11/1995 | (WO) . |

OTHER PUBLICATIONS

Damas, Chemical Abstracts, vol. 74, No. 19, Abstract No. 110,112y, May 1971.*

(List continued on next page.)

Primary Examiner—Zinna Northington Davis
(74) Attorney, Agent, or Firm—Nixon & Vanderhye P.C.

(57) ABSTRACT

A compound, compositions, methods of use, and processes of making formula I:

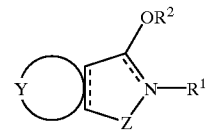

I or a pharmaceutically acceptable salt, hydrate, ester, solvate, prodrug, metabolite, stereoisomer, or mixtures thereof, wherein:

$R^1$, when present, is hydrogen or lower alkyl;

$R^2$ is lower alkyl, aryl, aralkyl, lower alkanoyl, or —$(CH_2)_n$—$(CHOH)_y(CH_2)_m$A, wherein n is 1–4, y is 0 or 1, m is 0–5, and A is cycloalkyl, cycloalkenyl, lower alkanoyl, aryl, aralkyl, —$NH_2$, —NH—(lower alkyl),

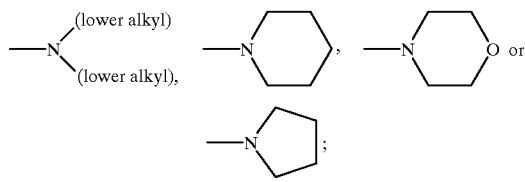

Y represents the atoms necessary to form a fused 5- to 6-membered ring that is aromatic or nonaromatic and carbocyclic or heterocyclic;

Z is (i) —$CHR^2CHR^3$— where $R^2$ and $R^3$ are independently hydrogen, alkyl, aryl or aralkyl;
(ii) —$R^6C$=$CR^3$— where $R^6$ and $R^3$ are independently hydrogen, lower alkyl, aryl, aralkyl, chlorine, bromine or —$NR^7R^8$, where $R^7$ and $R^8$ are independently hydrogen or lower alkyl, or, $R^6$ and $R^3$, taken together, form a fused 5- to 6-membered ring that is aromatic or nonaromatic and carbocyclic or heterocyclic;
(iii) —$R^2C$=N—;
(iv) —$CR^2(OH)$—$NR^7$—; or
(v) —$C(O)$—$NR^7$—.

23 Claims, 2 Drawing Sheets

OTHER PUBLICATIONS

A. Albert & J.N. Phillips, "Ionization Constants of Heterocyclic Substances. Part II. Hydroxy–derivatives of Nitrogenous Six–membered Ring–compounds", *Journal of the Chemical Society*, pp. 1294–1304 (1956).

M. Banasik et al., "Specific Inhibitors of Poly(ADP–Ribose) Synthetase and Mono (ADP–Ribosyl) transferase", *Journal of Biological Chemistry*, 267 (3) :1569–75 (Jan. 25, 1992).

Chemical Abstracts, vol. 52, No. 17, abstract No. 14606h ( Sep. 10, 1958).

Chemical Abstracts, vol. 55, No. 6, abstract No. 5491ce (Mar. 20, 1961).

Chemical Abstracts, vol. 58, No. 4, abstract No. 3425d (Feb. 18, 1963).

R. Griffin et al., "Novel Potent Inhibitors of the DNA Repair Enzyme Poly(ADP–Ribose) Polymerase (PARP)", *Anti–Cancer Drug Design*, 10 (6) :507–14 (Sep. 1995).

A. Nuvole & G. Pinna, "Synthesis of 1–Amino–4chloroisoquinoline. A New Approach to 1–Aminoisoquinoline", *Journal of Heterocyclic Chemistry*, vol. 15, pp. 1513–1514 (Dec. 1978).

M.J. Suto et al., "Dihydroisoquinolinones: The Design and Sythesis of a New Series of Potent Inhibitors of Poly(ADP–Ribose) Polymerase", *Anti–Cancer Drug Design*, vol. 7, pp. 107–117 (1991).

E. Taylor et al., "Nucleophilic Displacement of Primary Amino Groups via 1–Substituted 4 Tosylimidazoles", *Journal of Organic Chemistry*, 47 (11) :2043–6 (1982).

J. Wilson et al., "Local Anesthetics. Aminoalkoxyisoquinoline Derivatives", *Journal of the American Chemical Society*, vol. 71, pp. 937–938 (Mar. 1949).

H. Wright & M.B. Moore, "Local Anesthetics. V. 4–Morpholinylalkyl Aryl Ether", *Journal of the American Chemical Society*, vol. 76, pp. 4396–4398 (Sep. 5, 1954).

Desilets et al., "Design and Synthesis of Near–Infrared Absorbing Pigments", Can. J. Chem., 73, 319–35 (1995). (Part I and Part II).

Langlois et al., "Synthesis of Quinazoline–2, 4–dione and Naphthalimide Derivatives as New 5–HT3 Receptor Antagonists", Eur. J. Med. Chem., 29, 925–40 (1994).

Mao et al., "The inhibition of nitric oxide–activated poly (ADP–ribose) synthetase attenuates transsynaptic alteration of spinal cord dorsal horn neurons and neuropathic pain in the rat", Pain Vol. 72, pp. 355–366 (1997).

Purnell et al., "Novel Inhibitors of Poly (ADP–Ribose) Synthase", Biochem. J., 185, 775–77 (1980).

Ruf et al., "Structure of the catalytic fragment of poly (ADP–ribose) polymerase from chicken", Proc. Natl. Acad. Sci. USA vol. 93, pp. 7481–7485 (Jul. 1996).

Vaziri et al., "ATM—dependent telomere loss in aging human dipoloid fibroblasts and DNA damage lead to the post–translational activation of p53 protein involving poly (ADP–ribose) polymerase", The EMBO Journal vol. 16 No. 19, pp. 6018–6033 (1997).

Thiemermann et al. Proc. Natl. Acad Sci. USA 94:679–83 1997.

Iadecola Trends Neurosci. 20:3, 132–139 1997.

Dawson et al. Cerebrovascular Disease 319–25 1997.

White et al. Tetrahedron Letters 52:9, 3117–34 1996.

Dawson et al. J. Neurosci. 16:8, 2479–87 1996.

Zhang et al. J. Neurochem 65:3, 1411–14 1995.

White et al. Tetrahedron Letters 36:33, 5983–86 1995.

R. Griffin et al. Anti–Cancer Drug Design 10(6): 507–14 1995.

Zhang et al. Science 263:687–89 1994.

Huang et al. Science 265:1883–1885 1994.

Banasik et al. Molec. Cell Biochem. 138:185–97 1994.

Wallis et al. NeuroReport 5:3, 245–48 1993.

Dawson et al. J. Neurosci 13:6, 2651–61 1993.

Beckman et al. Biochemical Society Transactions 21:330–334 1993.

Dawson et al. Proc. Natl. Acad Sci. USA 88:6368–71 1991.

Milam et al. Science 223:589–91 1984.

Bauer et al., "Modification of Growth Related Enzymatic Pathways and Apparent Loss of Tumorigenicity of a ras–transformed Bovine Endothelial Cell Line by Treatment with 5–Iodo–6–amino–1,2–benzopyrone ($INH_2BP$)", *Intl. J. Oncol.*, 8:239–52 (1996).

Cosi et al., "Poly (ADP–Ribose) Polymerase (PARP) Revisited. A New Role for an Old Enzyme: PARP Involvement in Neurodegeneration and PARP Inhibitors as Possible Neuroprotective Agents", *Ann. N. Y. Acad. Sci.* 825:366–79 (1997).

Cosi et al., "Poly (ADP–Ribose) Polymerase Inhibitors Protect Against MPTP–induced Depletions of Striatal Dopamine and Cortical Noradrenaline in C57B1/6 Mice", *Brain Res.* 729:264–69 (1996).

Cristovao et al., "Effect of a Poly (ADP–Ribose) Polymerase Inhibitor on DNA Breakage and Cytotoxicity Induced by Hydrogen Peroxide and γ–Radiation", *Terato., Carcino., and Muta.*, 16:219–27 (1996).

Cuzzocrea, "Role of Peroxynitrite and Activation of Poly (ADP–Ribose) Synthetase in the Vascular Failure Induced by Zymosan–activated Plasma", *Brit. J. Pharm.*, 122:493–503 (1997).

Endres et al., "Ischemic Brain Injury is Mediated by the Activation of Poly (ADP–Ribose) Polymerase," *J. Cerebral Flood Flow Metabol.*, 17 (11) :1143–51 (1997).

Heller et al., "Inactivation of the Poly (ADP–Ribose) Polymerase Gene Affects Oxygen Radical and Nitric Oxide Toxicity in Islet Cells", *J. Biol. Chem.*, 270:11176–80 (1995).

Hughes et al., "Induction of T Helper Cell Hyporesponsiveness in an Experimental Model of Autoimmunity by Using Nonmitogenic Anti–CD3 Monoclonal Antibody", *J. Immuno.*, 153:3319–25 (1994).

Salzman et al., "Role of Peroxynitrite and Poly (ADP–Ribose) Synthase Activation Experimental Colitis", *Japanese J. Pharm.*, 75, Supp. I:15 (1997).

Southan et al., "Spontaneous Rearrangement of Aminoalkylisothioureas into Mercaptoalkylguanidines, a Novel Class of Nitric Oxide Synthase Inhibitors with Selectivity Towards the Inducible Isoform", *Br. J. Pharm.*, 117:619–32 (1996).

Szabó et al., "DNA Strand Breakage, Activation of Poly (ADP–Ribose) Synthetase, and Cellular Energy Depletion are Involved in the Cytotoxicity in Macrophages and Smooth Muscle Cells Exposed to Peroxynitrite", *Proc. Natl. Acad. Sci. USA*, 93:1753–58 (1996).

Szabó et al., "Mercaptoethylguanidine and Guanidine Inhibitors of Nitric Oxide Synthase React with peroxynitrite and Protect Against Peroxynitrite–induced Oxidative Damage", *J. Biol. Chem.*, 272:9030–36 (1997).

Szabó et al., "Protective Effects of an Inhibitor of Poly (ADP–Ribose) Synthetase in Collagen–Induced Arthritis," *Japanese J. Pharm.*, 75, Supp. I:102 (1997).

Wallis et al., Traumatic Neuroprotection with Inhibitors of Nitric Oxide and ADP–Ribosylation, *Brain Res.*, 710:169–77 (1996).

Weltin et al., "Effect of 6($5_H$)–Phenanthridinone, and Inhibitor of Poly (ADP–ribose) Polymerase, on Cultured Tumor Cells", *Oncol. Res.*, 6:399–403 (1994).

Zingarelli et al., "Protective Effects of Nicontinamide Against Nitric Oxide—Mediated Delayed Vascular Failure in Endotoxic Shock: Potential Involvement of PolyADP Ribosyl Synthetase", *Shock*, 5:258–64 (1996).

* cited by examiner

ALKOXY-SUBSTITUTED COMPOUNDS, METHODS, AND COMPOSITIONS FOR INHIBITING PARP ACTIVITY

This application is a continuation-in-part application of U.S. patent application Ser. No. 09/079,508, filed May 15, 1998, now pending and also of U.S. patent application Ser. No. 08/922,520, filed Sep. 3, 1997, now abandoned the contents of which are incorporated herein in their entirety.

BACKGROUND OF THE INVENTION

1. Field of the Invention

The present invention relates to inhibitors of the nucleic enzyme poly(adenosine 5'-diphospho-ribose) polymerase ["poly(ADP-ribose) polymerase" or "PARP", which is also sometimes called "PARS" for poly(ADP-ribose) synthetase]. More particularly, the invention relates to the use of PARP inhibitors to prevent and/or treat tissue damage resulting from cell damage or death due to necrosis or apoptosis; neural tissue damage resulting from ischemia and reperfusion injury; neurological disorders and neurodegenerative diseases; to prevent or treat vascular stroke; to treat or prevent cardiovascular disorders; to treat other conditions and/or disorders such as age-related macular degeneration, AIDS and other immune senescence diseases, arthritis, atherosclerosis, cachexia, cancer, degenerative diseases of skeletal muscle involving replicative senescence, diabetes, head trauma, immune senescence, inflammatory bowel disorders (such as colitis and Crohn's disease), muscular dystrophy, osteoarthritis, osteoporosis, chronic and acute pain (such as neuropathic pain), renal failure, retinal ischemia, septic shock (such as endotoxic shock), and skin aging; to extend the lifespan and proliferative capacity of cells; to alter gene expression of senescent cells; or to radiosensitize hypoxic tumor cells.

2. Description of the Prior Art

Poly(ADP-ribose) polymerase ("PARP") is an enzyme located in the nuclei of cells of various organs, including muscle, heart and brain cells. PARP plays a physiological role in the repair of strand breaks in DNA. Once activated by damaged DNA fragments, PARP catalyzes the attachment of up to 100 ADP-ribose units to a variety of nuclear proteins, including histones and PARP itself. While the exact range of functions of PARP has not been fully established, this enzyme is thought to play a role in enhancing DNA repair.

During major cellular stresses, however, the extensive activation of PARP can rapidly lead to cell damage or death through depletion of energy stores. Four molecules of ATP are consumed for every molecule of NAD (the source of ADP-ribose) regenerated. Thus, NAD, the substrate of PARP, is depleted by massive PARP activation and, in the efforts to re-synthesize NAD, ATP may also be depleted.

It has been reported that PARP activation plays a key role in both NMDA- and NO-induced neurotoxicity, as shown by the use of PARP inhibitors to prevent such toxicity in cortical cultures in proportion to their potencies as inhibitors of this enzyme (Zhang et al., "Nitric Oxide Activation of Poly(ADP-Ribose) Synthetase in Neurotoxicity", *Science*, 263:687–89 (1994)); and in hippocampal slices (Wallis et al., "Neuroprotection Against Nitric Oxide Injury with Inhibitors of ADP-Ribosylation", *NeuroReport*, 5:3, 245–48 (1993)). The potential role of PARP inhibitors in treating neurodegenerative diseases and head trauma has thus been known. Research, however, continues to pinpoint the exact mechanisms of their salutary effect in cerebral ischemia, (Endres et al., "Ischemic Brain Injury is Mediated by the Activation of Poly(ADP-Ribose)Polymerase", *J. Cereb. Blood Flow Metabol.*, 17:1143–51 (1997)) and in traumatic brain injury (Wallis et al., "Traumatic Neuroprotection with Inhibitors of Nitric Oxide and ADP-Ribosylation, *Brain Res.*, 710:169–77 (1996)).

It has been demonstrated that single injections of PARP inhibitors have reduced the infarct size caused by ischemia and reperfusion of the heart or skeletal muscle in rabbits. In these studies, a single injection of the PARP inhibitor, 3-amino-benzamide (10 mg/kg), either one minute before occlusion or one minute before reperfusion, caused similar reductions in infarct size in the heart (32–42%). Another PARP inhibitor, 1,5-dihydroxyisoquinoline (1 mg/kg), reduced infarct size by a comparable degree (38–48%). Thiemermann et al., "Inhibition of the Activity of Poly(ADP Ribose) Synthetase Reduces Ischemia-Reperfusion Injury in the Heart and Skeletal Muscle", *Proc. Natl. Acad. Sci. USA*, 94:679–83 (1997). This finding has suggested that PARP inhibitors might be able to salvage previously ischemic heart or skeletal muscle tissue.

PARP activation has also been shown to provide an index of damage following neurotoxic insults by glutamate (via NMDA receptor stimulation), reactive oxygen intermediates, amyloid β-protein, n-methyl-4-phenyl-1,2,3, 6-tetrahydropyridine (MPTP) and its active metabolite N-methyl-4-phenylpyridine (MPP$^+$), which participate in pathological conditions such as stroke, Alzheimer's disease and Parkinson's disease. Zhang et al., "Poly(ADP-Ribose) Synthetase Activation: An Early Indicator of Neurotoxic DNA Damage", *J. Neurochem.*, 65:3, 1411–14 (1995). Other studies have continued to explore the role of PARP activation in cerebellar granule cells in vitro and in MPTP neurotoxicity. Cosi et al., "Poly(ADP-Ribose) Polymerase (PARP) Revisited. A New Role for an Old Enzyme: PARP Involvement in Neurodegeneration and PARP Inhibitors as Possible Neuroprotective Agents", *Ann. N.Y. Acad. Sci.*, 825:366–79 (1997); and Cosi et al., "Poly(ADP-Ribose) Polymerase Inhibitors Protect Against MPTP-induced Depletions of Striatal Dopamine and Cortical Noradrenaline in C57B1/6 Mice", *Brain Res.*, 729:264–69 (1996).

Neural damage following stroke and other neurodegenerative processes is thought to result from a massive release of the excitatory neurotransmitter glutamate, which acts upon the N-methyl-D-aspartate (NMDA) receptors and other subtype receptors. Glutamate serves as the predominate excitatory neurotransmitter in the central nervous system (CNS). Neurons release glutamate in great quantities when they are deprived of oxygen, as may occur during an ischemic brain insult such as a stroke or heart attack. This excess release of glutamate in turn causes over-stimulation (excitotoxicity) of N-methyl-D-aspartate (NMDA), AMPA, Kainate and MGR receptors. When glutamate binds to these receptors, ion channels in the receptors open, permitting flows of ions across their cell membranes, e.g., $Ca^{2+}$ and $Na^+$ into the cells and $K^+$ out of the cells. These flows of ions, especially the influx of $Ca^{2+}$, cause overstimulation of the neurons. The over-stimulated neurons secrete more glutamate, creating a feedback loop or domino effect which ultimately results in cell damage or death via the production of proteases, lipases and free radicals. Excessive activation of glutamate receptors has been implicated in various neurological diseases and conditions including epilepsy, stroke, Alzheimer's disease, Parkinson's disease, Amyotrophic Lateral Sclerosis (ALS), Huntington's disease, schizophrenia, chronic pain, ischemia and neuronal loss following hypoxia, hypoglycemia, ischemia, trauma, and nervous insult. Recent studies have also advanced a glutamatergic basis for compulsive disorders, particularly drug dependence. Evidence includes findings in many animal species, as well as, in cerebral cortical cultures treated with glutamate or NMDA, that glutamate receptor antagonists block neural damage following vascular stroke. Dawson et al., "Protection of the Brain from Ischemia", *Cerebrovascular Disease*, 319–25 (H. Hunt Batjer ed., 1997). Attempts to prevent excitotoxicity by blocking NMDA, AMPA, Kainate and MGR receptors have proven difficult because each receptor has multiple sites to which glutamate may bind. Many of the compositions that are effective in blocking the receptors are also toxic to animals. As such, there is no known effective treatment for glutamate abnormalities.

The stimulation of NMDA receptors, in turn, activates the enzyme neuronal nitric oxide synthase (NNOS), which causes the formation of nitric oxide (NO), which more directly mediates neurotoxicity. Protection against NMDA neurotoxicity has occurred following treatment with NOS inhibitors. See Dawson et al., "Nitric Oxide Mediates Glutamate Neurotoxicity in Primary Cortical Cultures", *Proc. Natl. Acad. Sci. USA*, 88:6368–71 (1991); and Dawson et al., "Mechanisms of Nitric Oxide-mediated Neurotoxicity in Primary Brain Cultures", *J. Neurosci.*, 13:6, 2651–61 (1993). Protection against NMDA neurotoxicity can also occur in cortical cultures from mice with targeted disruption of NNOS. See Dawson et al., "Resistance to Neurotoxicity in Cortical Cultures from Neuronal Nitric Oxide Synthase-Deficient Mice", *J. Neurosci.*, 16:8, 2479–87 (1996).

It is known that neural damage following vascular stroke is markedly diminished in animals treated with NOS inhibitors or in mice with NNOS gene disruption. Iadecola, "Bright and Dark Sides of Nitric Oxide in Ischemic Brain Injury", *Trends Neurosci.*, 20:3, 132–39 (1997); and Huang et al., "Effects of Cerebral Ischemia in Mice Deficient in Neuronal Nitric Oxide Synthase", *Science*, 265:1883–85 (1994). See also, Beckman et al., "Pathological Implications of Nitric Oxide, Superoxide and Peroxynitrite Formation", *Biochem. Soc. Trans.*, 21:330–34 (1993). Either NO or peroxynitrite can cause DNA damage, which activates PARP. Further support for this is provided in Szabó et al., "DNA Strand Breakage, Activation of Poly(ADP-Ribose) Synthetase, and Cellular Energy Depletion are Involved in the Cytotoxicity in Macrophages and Smooth Muscle Cells Exposed to Peroxynitrite", *Proc. Natl. Acad. Sci. USA*, 93:1753–58 (1996).

Zhang et al., U.S. Pat. No. 5,587,384 issued Dec. 24, 1996, discusses the use of certain PARP inhibitors, such as benzamide and 1,5-dihydroxy-isoquinoline, to prevent NMDA-mediated neurotoxicity and, thus, treat stroke, Alzheimer's disease, Parkinson's disease and Huntington's disease. However, it is has now been discovered that Zhang et al. may have been in error in classifying neurotoxicity as NMDA-mediated neurotoxicity. Rather, it may have been more appropriate to classify the in vivo neurotoxicity present as glutamate neurotoxicity. See Zhang et al. "Nitric Oxide Activation of Poly(ADP-Ribose) Synthetase in Neurotoxicity", *Science*, 263:687–89 (1994). See also, Cosi et al., Poly(ADP-Ribose)Polymerase Inhibitors Protect Against MPTP-induced Depletions of Striatal Dopamine and Cortical Noradrenaline in C57B1/6 Mice", *Brain Res.*, 729:264–69 (1996).

It is also known that PARP inhibitors affect DNA repair generally. Cristovao et al., "Effect of a Poly(ADP-Ribose) Polymerase Inhibitor on DNA Breakage and Cytotoxicity Induced by Hydrogen Peroxide and γ-Radiation," *Terato., Carcino., and Muta.*, 16:219–27 (1996), discusses the effect of hydrogen peroxide and γ-radiation on DNA strand breaks in the presence of and in the absence of 3-aminobenzamide, a potent inhibitor of PARP. Cristovao et al. observed a PARP-dependent recovery of DNA strand breaks in leukocytes treated with hydrogen peroxide.

PARP inhibitors have been reported to be effective in radiosensitizing hypoxic tumor cells and effective in preventing tumor cells from recovering from potentially lethal damage of DNA after radiation therapy, presumably by their ability to prevent DNA repair. See U.S. Pat. Nos. 5,032,617; 5,215,738; and 5,041,653.

Evidence also exists that PARP inhibitors are useful for treating inflammatory bowel disorders. Salzman et al., "Role of Peroxynitrite and Poly(ADP-Ribose)Synthase Activation Experimental Colitis," *Japanese J. Pharm.*, 75, Supp. I:15 (1997), discusses the ability of PARP inhibitors to prevent or treat colitis. Colitis was induced in rats by intraluminal administration of the hapten trinitrobenzene sulfonic acid in 50% ethanol. Treated rats received 3-aminobenzamide, a specific inhibitor of PARP activity. Inhibition of PARP activity reduced the inflammatory response and restored the morphology and the energetic status of the distal colon. See also, Southan et al., "Spontaneous Rearrangement of Aminoalkylithioureas into Mercaptoalkylguanidines, a Novel Class of Nitric Oxide Synthase Inhibitors with Selectivity Towards the Inducible Isoform", *Br. J. Pharm.*, 117:619–32 (1996); and Szabó et al., "Mercaptoethylguanidine and Guanidine Inhibitors of Nitric Oxide Synthase React with Peroxynitrite and Protect Against Peroxynitrite-induced Oxidative Damage", *J. Biol. Chem.*, 272:9030–36 (1997).

Evidence also exists that PARP inhibitors are useful for treating arthritis. Szabó et al., "Protective Effects of an Inhibitor of Poly(ADP-Ribose)Synthetase in Collagen-Induced Arthritis," *Japanese J. Pharm.*, 75, Supp. I:102 (1997), discusses the ability of PARP inhibitors to prevent or treat collagen-induced arthritis. See also Szabó et al., "DNA Strand Breakage, Activation of Poly(ADP-Ribose) Synthetase, and Cellular Energy Depletion are Involved in the Cytotoxicity in Macrophages and Smooth Muscle Cells Exposed to Peroxynitrite," *Proc. Natl. Acad. Sci. USA*, 93:1753–58 (March 1996); Bauer et al., "Modification of Growth Related Enzymatic Pathways and Apparent Loss of Tumorigenicity of a ras-transformed Bovine Endothelial Cell Line by Treatment with 5-Iodo-6-amino-1,2-benzopyrone (INH$_2$BP)", *Intl. J. Oncol.*, 8:239–52 (1996), and Hughes et al., "Induction of T Helper Cell Hyporesponsiveness in an Experimental Model of Autoimmunity by Using Nonmitogenic Anti-CD3 Monoclonal Antibody", *J. Immuno.*, 153:3319–25 (1994).

Further, PARP inhibitors appear to be useful for treating diabetes. Heller et al., "Inactivation of the Poly(ADP-Ribose)Polymerase Gene Affects Oxygen Radical and Nitric Oxide Toxicity in Islet Cells," *J. Biol. Chem.*, 270:19, 11176–80 (May 1995), discusses the tendency of PARP to deplete cellular NAD+ and induce the death of insulin-producing islet cells. Heller et al. used cells from mice with inactivated PARP genes and found that these mutant cells did not show NAD+ depletion after exposure to DNA-damaging radicals. The mutant cells were also found to be more resistant to the toxicity of NO.

Further still, PARP inhibitors have been shown to be useful for treating endotoxic shock or septic shock. Zingarelli et al., "Protective Effects of Nicotinamide Against Nitric Oxide-Mediated Delayed Vascular Failure in Endotoxic Shock: Potential Involvement of PolyADP Ribosyl Synthetase," *Shock*, 5:258–64 (1996), suggests that inhibition of the DNA repair cycle triggered by poly(ADP ribose) synthetase has protective effects against vascular failure in endotoxic shock. Zingarelli et al. found that nicotinamide protects against delayed, NO-mediated vascular failure in endotoxic shock. Zingarelli et al. also found that the actions of nicotinamide may be related to inhibition of the NO-mediated activation of the energy-consuming DNA repair cycle, triggered by poly(ADP ribose) synthetase. See also, Cuzzocrea, "Role of Peroxynitrite and Activation of Poly(ADP-Ribose) Synthetase in the Vascular Failure Induced by Zymosan-activated Plasma," *Brit. J. Pharm.*, 122:493–503 (1997).

Yet another known use for PARP inhibitors is treating cancer. Suto et al., "Dihydroisoquinolinones: The Design and Synthesis of a New Series of Potent Inhibitors of Poly(ADP-Ribose) Polymerase", *Anticancer Drug Des.*, 7:107–17 (1991), discloses processes for synthesizing a number of different PARP inhibitors. In addition, Suto et al., U.S. Pat. No. 5,177,075, discusses several isoquinolines used for enhancing the lethal effects of ionizing radiation or chemotherapeutic agents on tumor cells. Weltin et al., "Effect of 6(5H)-Phenanthridinone, an Inhibitor of Poly (ADP-ribose) Polymerase, on Cultured Tumor Cells", *Oncol. Res.*, 6:9, 399–403 (1994), discusses the inhibition of PARP activity, reduced proliferation of tumor cells, and a marked synergistic effect when tumor cells are co-treated with an alkylating drug.

Still another use for PARP inhibitors is the treatment of peripheral nerve injuries, and the resultant pathological pain syndrome known as neuropathic pain, such as that induced by chronic constriction injury (CCI) of the common sciatic nerve and in which transsynaptic alteration of spinal cord dorsal horn characterized by hyperchromatosis of cytoplasm and nucleoplasm (so-called "dark" neurons) occurs. See Mao et al., *Pain*, 72:355–366 (1997).

PARP inhibitors have also been used to extend the lifespan and proliferative capacity of cells including treatment of diseases such as skin aging, Alzheimer's disease, atherosclerosis, osteoarthritis, osteoporosis, muscular dystrophy, degenerative diseases of skeletal muscle involving replicative senescence, age-related macular degeneration, immune senescence, AIDS, and other immune senescence diseases; and to alter gene expression of senescent cells. See WO 98/27975.

Large numbers of known PARP inhibitors have been described in Banasik et al., "Specific Inhibitors of Poly (ADP-Ribose) Synthetase and Mono(ADP-Ribosyl)-Transferase", *J. Biol. Chem.*, 267:3, 1569–75 (1992), and in Banasik et al., "Inhibitors and Activators of ADP-Ribosylation Reactions", *Molec. Cell. Biochem.*, 138:185–97 (1994).

However, the approach of using these PARP inhibitors in the ways discussed above has been limited in effect. For example, side effects have been observed with some of the best-known PARP inhibitors, as discussed in Milam et al., "Inhibitors of Poly(Adenosine Diphosphate-Ribose) Synthesis: Effect on Other Metabolic Processes", *Science*, 223:589–91 (1984). Specifically, the PARP inhibitors 3-aminobenzamide and benzamide not only inhibited the action of PARP but also were shown to affect cell viability, glucose metabolism, and DNA synthesis. Thus, it was concluded that the usefulness of these PARP inhibitors may be severely restricted by the difficulty of finding a dose that will inhibit the enzyme without producing additional metabolic effects.

Accordingly, there remains a need for compounds that inhibit PARP activity, compositions containing those compounds and methods utilizing those compounds, wherein the compounds produce more potent and reliable effects with fewer side effects, with respect to inhibiting PARP activity and treating the diseases and conditions discussed herein.

Further, other multicyclic, nitrogen-containing, alkoxy-substituted compounds are known:

1,3-Dihydro-4-methoxy-thieno[3,4-c]quinoline, which has the following structure:

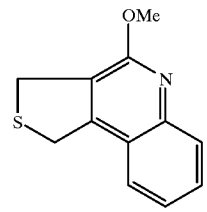

is disclosed in White et al., "Quinoline Analogues of Ortho-Quinodimethane," *Tetrahedron Letters*, 36:33, 5983–86 (1995). This structure is also disclosed in White et al., "Dihydrothiophenes as Precursors to Fused Quinolines, Quinolones and Coumarins via o-Quinodimethane Intermediates," *Tetrahedron Letters*, 52:9, 3117–34 (1996). Both of the White references also disclose the following structures:

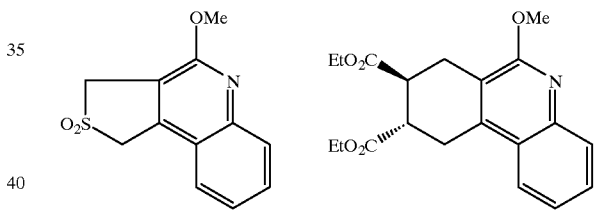

It is not believed that the above disclosed compounds have been shown to inhibit PARP activity per se.

SUMMARY OF THE INVENTION

The compounds of the present invention have formula I:

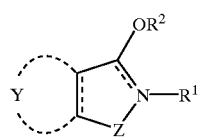

or a pharmaceutically acceptable salt, hydrate, ester, solvate, prodrug, metabolite, stereoisomer, or mixtures thereof, wherein:

$R^1$, when present, is hydrogen or lower alkyl;

$R^2$ is lower alkyl, aryl, aralkyl, lower alkanoyl, or —$(CH_2)_n$—$(CHOH)_y(CH_2)_m$A, wherein n is 1–4, y is 0 or 1, m is 0–5, and A is cycloalkyl, cycloalkenyl, lower alkanoyl, aryl, aralkyl, —$NH_2$, —NH—(lower alkyl),

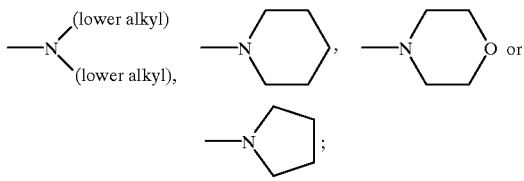

Y represents the atoms necessary to form a fused 5- to 6-membered ring that is aromatic or nonaromatic and carbocyclic or heterocyclic;

Z is (i) —CHR²CHR³— where R² and R³ are independently hydrogen, alkyl, aryl or aralkyl;

(ii) —R⁶C═CR³— where R⁶ and R³ are independently hydrogen, lower alkyl, aryl, aralkyl, chlorine, bromine or —NR⁷R⁸, where R⁷ and R⁸ are independently hydrogen or lower alkyl, or, R⁶ and R³, taken together, form a fused 5- to 6-membered ring that is aromatic or nonaromatic and carbocyclic or heterocyclic;

(iii) —R²C═N—;
(iv) —CR²(OH)—NR⁷—; or
(v) —C(O)—NR⁷—;

provided that when R⁶ and R³ form a fused benzene ring, then Y is neither (a) a fused, 6-membered, nonaromatic carbocyclic ring nor (b) a fused, 5-membered, nonaromatic heterocyclic ring having a sulfur atom as its sole heteroatom.

In another embodiment, a process of making the compound of formula I:

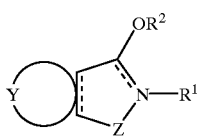

I or a pharmaceutically acceptable salt, hydrate, ester, solvate, prodrug, metabolite, stereoisomer, or mixtures thereof, wherein R¹, R², n, y, m, A, Y, Z, R⁶, R³, R⁷, and R⁸ are as defined above, comprises the step of contacting an intermediate having formula II:

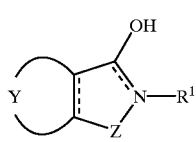

II with R₁X wherein X is a bromo, chloro or iodo moiety.

In yet another embodiment, the pharmaceutical composition of the invention comprises a pharmaceutically acceptable carrier and a compound of formula I:

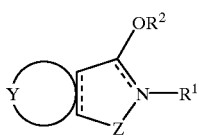

I or a pharmaceutically acceptable salt, hydrate, ester, solvate, prodrug, metabolite, stereoisomer, or mixtures thereof, wherein:

R¹, when present, is hydrogen or lower alkyl;

R² is lower alkyl, aryl, aralkyl, lower alkanoyl, or —(CH₂)ₙ—(CHOH)ᵧ(CH₂)ₘA, wherein n is 1–4, y is 0 or 1, m is 0–5, and A is cycloalkyl, cycloalkenyl, lower alkanoyl, aryl, aralkyl, —NH₂, —NH—(lower alkyl),

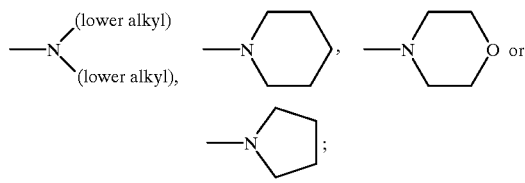

Y represents the atoms necessary to form a fused 5- to 6-membered ring that is aromatic or nonaromatic and carbocyclic or heterocyclic;

Z is (i) —CHR²CHR— where R² and R³ are independently hydrogen, alkyl, aryl or aralkyl;

(ii) —R⁶C═CR³— where R⁶ and R³ are independently hydrogen, lower alkyl, aryl, aralkyl, chlorine, bromine or —NR⁷R⁸, where R⁷ and R⁸ are independently hydrogen or lower alkyl, or, R⁶ and R³, taken together, form a fused 5- to 6-membered ring that is aromatic or nonaromatic and carbocyclic or heterocyclic;

(iii) —R²C═N—;
(iv) —CR²(OH)—NR⁷—; or
(v) —C(O)—NR⁷—;

provided that when R⁶ and R³ form a fused benzene ring, then Y is neither (a) a fused, 6-membered, nonaromatic carbocyclic ring nor (b) a fused, 5-membered, nonaromatic heterocyclic ring having a sulfur atom as its sole heteroatom.

In particularly preferred embodiments of the above composition, the amount of the compound of formula I is present in an amount effective to inhibit PARP activity, to treat or prevent tissue damage regulting from cell damage or death due to necrosis or apoptosis, to effect a neuronal activity not mediated by NMDA toxicity, to effect a neuronal activity mediated by NMDA toxicity, to treat neural tissue damage resulting from ischemia and reperfusion injury, neurological disorders and neurodegenerative diseases; to prevent or treat vascular stroke; to treat or prevent cardiovascular disorders; to treat other conditions and/or disorders such as age-related macular degeneration, AIDS and other immune senescence diseases, arthritis, atherosclerosis, cachexia, cancer, degenerative diseases of skeletal muscle involving replicative senescence, diabetes, head trauma, immune senescence, inflammatory bowel disorders (such as colitis and Crohn's disease), muscular dystrophy, osteoarthritis, osteoporosis, chronic and/or acute pain (such as neuropathic pain), renal failure, retinal ischemia, septic shock (such as endotoxic shock), and skin aging; to extend the lifespan and proliferative capacity of cells; to alter gene expression of senescent cells; or to radiosensitize hypoxic tumor cells.

In an additional embodiments, a method of inhibiting PARP activity comprises administering a compound of formula I, as described above for the pharmaceutical compositions of the invention. In preferred embodiments, the amount of the compound administered in the methods of the invention is effective for treating tissue damage resulting from cell damage or death due to necrosis or apoptosis, neural tissue damage resulting from ischemia and reperfusion injury, or neurological disorders and neurodegenerative diseases; to prevent or treat vascular stroke; to treat or prevent cardiovascular disorders; to treat other conditions and/or disorders such as age-related macular degeneration, AIDS and other immune senescence diseases, arthritis, atherosclerosis, cachexia, cancer, degenerative diseases of skeletal muscle involving replicative senescence, diabetes, head trauma, immune senescence, inflammatory bowel disorders (such as colitis and Crohn's disease), muscular dystrophy, osteoarthritis, osteoporosis, chronic and/or acute pain (such as neuropathic pain), renal failure, retinal ischemia, septic shock (such as endotoxic shock), and skin aging; to extend the lifespan and proliferative capacity of cells; to alter gene expression of senescent cells; or to radiosensitive hypoxic tumor cells.

DETAILED DESCRIPTION OF THE INVENTION

Figure 1:
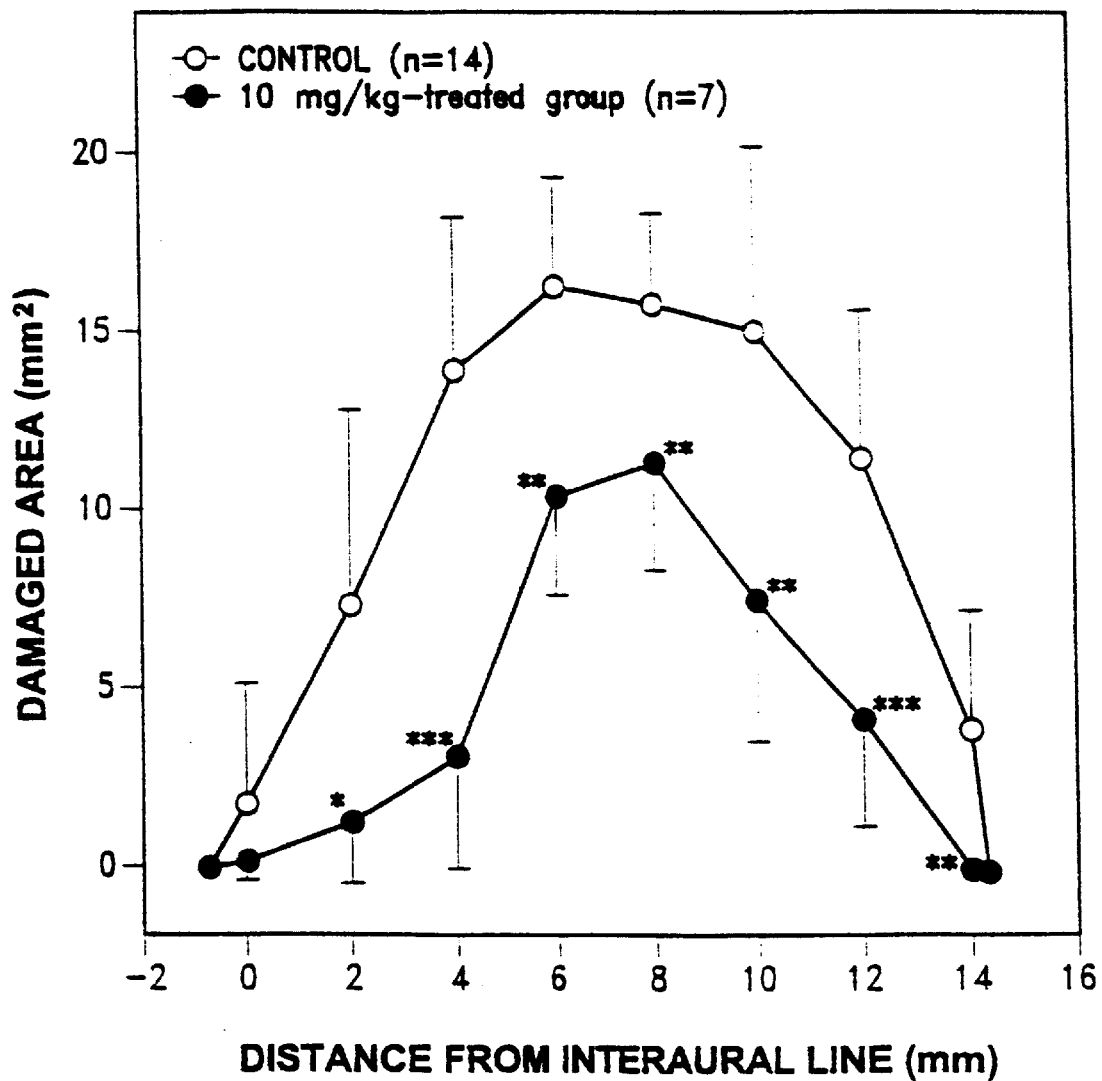
FIG. 1 shows the distribution of the cross-sectional infarct area at representative levels along the rostrocaudal axis, as measured from the interaural line in non-treated animals and in animals treated with 10 mg/kg of 3,4-dihydro-5-[4-(1-piperidinyl)-butoxyl]-1(2H)-isoquinolinone.

The alkoxy-substituted compounds of the present invention inhibit PARP activity. As such, they may treat or prevent neural tissue damage resulting from cell damage or death due to necrosis or apoptosis, cerebral ischemia and reperfusion injury or neurodegenerative diseases in an animal; they may extend the lifespan and proliferative capacity of cells and thus be used to treat or prevent diseases associated therewith; they may alter gene expression of senescent cells; and they may radiosensitize hypoxic tumor cells. Preferably, the compounds of the invention treat or prevent tissue damage resulting from cell damage or death due to necrosis or apoptosis, and/or effect neuronal activity, either mediated or not mediated by NMDA toxicity. These compounds are thought to interfere with more than the glutamate neurotoxicity and NO-mediated biological pathways. Further, the compounds of the invention can treat or prevent other tissue damage related to PARP activation.

For example, the compounds of the invention can treat or prevent cardiovascular tissue damage resulting from cardiac ischemia or reperfusion injury. Reperfusion injury, for instance, occurs at the termination of cardiac bypass procedures or during cardiac arrest when the heart, once prevented from receiving blood, begins to reperfuse.

The compounds of the present invention can also be used to extend or increase the lifespan or proliferation of cells and thus to treat or prevent diseases associated therewith and induced or exacerbated by cellular senescence including skin aging, atherosclerosis, osteoarthritis, osteoporosis, muscular dystrophy, degenerative diseases of skeletal muscle involving replicative senescence, age-related macular degeneration, immune senescence, AIDS and other immune senescence diseases, and other diseases associated with cellular senescence and aging, as well as to alter the gene expression of senescent cells. These compounds can also be used to treat cancer and to radiosensitize hypoxic tumor cells to render the tumor cells more susceptible to radiation therapy and to prevent the tumor cells from recovering from potentially lethal damage of DNA after radiation therapy, presumably by their ability to prevent DNA repair. The compounds of the present invention can be used to prevent or treat vascular stroke; to treat or prevent cardiovascular disorders; to treat other conditions and/or disorders such as age-related macular degeneration, AIDS and other immune senescence diseases, arthritis, atherosclerosis, cachexia, cancer, degenerative diseases of skeletal muscle involving replicative senescence, diabetes, head trauma, immune senescence, inflammatory bowel disorders (such as colitis and Crohn's disease), muscular dystrophy, osteoarthritis, osteoporosis, chronic and/or acute pain (such as neuropathic pain), renal failure, retinal ischemia, septic shock (such as endotoxic shock), and skin aging.

Preferably, the compounds of the invention act as PARP inhibitors to treat or prevent tissue damage resulting from cell death or damage due to necrosis or apoptosis; to treat or prevent neural tissue damage resulting from cerebral ischemia and reperfusion injury or neurodegenerative diseases in an animal; to extend and increase the lifespan and proliferative capacity of cells; to alter gene expression of senescent cells; and to radiosensitize tumor cells. These compounds are thought to interfere with more than the NMDA-neurotoxicity and NO-mediated biological pathways. Preferably, the compounds of the invention exhibit an $IC_{50}$ for inhibiting PARP in vitro of about 100 $\mu$M or lower, more preferably, about 25 $\mu$M or lower.

The inventors have now discovered that select alkoxy-substituted compounds that inhibit PARP activity can ameliorate neural tissue damage, including that following focal ischemia and reperfusion injury; can increase or extend the lifespan or proliferation of cells; can alter gene expression in senescent cells; and can radiosensitize tumor cells. Generally, inhibition of PARP activity spares the cell from energy loss, preventing irreversible depolarization of the neurons and, thus, provides neuroprotection. While not wishing to be bound thereby, it is thought that PARP activation may play a common role in still other excitotoxic mechanisms, perhaps as yet undiscovered, in addition to the production of free radicals and NO. Since PARP is necessary for DNA repair, the inhibition of PARP can also be used to prevent radiation damaged tumor cells from recovering from potentially lethal damage of DNA by preventing DNA repair. PARP inhibitors may also be used to extend or increase the lifespan and proliferation of cells and to thus prevent or treat diseases and conditions associated with cellular senescence, and can be used to alter the gene expression of senescent cells can increase or extend the lifespan or proliferation of cells; can alter gene expression in senescent cells; and can radiosensitize tumor cells.

The compounds of the invention act as PARP inhibitors to treat or prevent neural tissue damage resulting from cerebral ischemia and reperfusion injury or neuro-degenerative diseases in an animal; to extend and increase the lifespan and proliferative capacity of cells; to alter gene expression of senescent cell; and to radiosensitize tumor cells. These compounds are thought to interfere with more than the NMDA-neurotoxicity and NO-mediated biological pathways. Preferably, the compounds of the invention exhibit an $IC_{50}$ for inhibiting PARP in vitro of about 100 $\mu$M or lower, more preferably, about 25 $\mu$M or lower.

The compound of the invention has the formula:

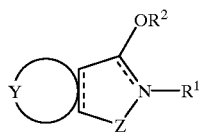

I or a pharmaceutically acceptable salt, hydrate, ester, solvate, prodrug, metabolite, stereoisomer or mixtures thereof, wherein Y represents the atoms necessary to form a fused 5- to 6-membered ring that is aromatic or nonaromatic and carbocyclic or heterocyclic.

When Y forms a fused 5-membered carbocyclic ring, examples thereof include such rings as fused cyclopentane, cyclopentene, cyclopentadiene rings and the like. When Y forms a 5-membered N-containing heterocyclic ring, examples thereof include such rings as fused pyrrole, isopyrrole, imidazole, isoimidazole, pyrazole, pyrrolidine, pyrroline, imidazolidine, imidazoline, pyrazolidine, pyrazoline, isothiazole, isoxazole, furazan, furan, thiophene, 1,2,3-triazole, 1,2,4-triazole, dithiole, oxathiole, isoxazole, oxazole, thiazole, isothiazole, oxadiazole, omatriazole, dioxazole, oxathiazole and the like rings.

When Y forms a fused 6-membered carbocyclic ring, examples of useful Y groups include a fused cyclohexane, cyclohexene, benzene or the like, optionally substituted with additional fused rings, thus forming, for example, naphthalene, anthracene, phenanthrene, benzonaphthene, and the like ring systems.

When Y forms a 6-membered N-containing heterocyclic ring, examples thereof include such rings as pyridine, pyrazine, pyrimidine, pyridazine, piperidine, piperazine, morpholine, pyran, pyrone, dioxin, triazine, oxazine, isoxazine, oxathiazine, oxadiazine, and the like rings.

Y may be aromatic, such as pyrrole, benzene or pyridine; or non-aromatic, such as cyclopentene, piperidyl or piperazinyl. Preferably, Y has at least one site of unsaturation.

Y may be unsubstituted or substituted with one or more non-interfering substituents. For example, Y may be substituted with an alkyl group such as methyl, ethyl, propyl, butyl, pentyl, hexyl, isopropyl, isobutyl, tert-butyl, n-pentyl, 2-methylpentyl, 2-methylhexyl, dodecyl, octadecyl and the like; with an alkenyl group such as ethenyl, propenyl, butenyl, pentenyl, 2-methylpentenyl, vinyl, isopropenyl, 2,2-dimethyl-1-propenyl, decenyl, hexadecenyl and the like; with an alkynyl group such as ethynyl, propynyl, butynyl, pentynyl, hexynyl, heptynyl, octynyl and the like; with an alkanoyl group such as formyl, acetyl, propanoyl, butanoyl, pentanoyl, benzoyl and the like; with a cycloalkyl group such as adamantyl, cyclobutyl, cyclopentyl, cyclohexyl, cycloheptyl, cyclooctanyl, cyclononyl, cyclodecyl and the like; with a cycloalkenyl group such as cyclopropenyl, cyclopentadienyl, cyclohexenyl, cyclooctenyl and the like; with an aralkyl group such as benzyl, 3-(1)-naphthyl-1-propyl, p-halobenzyl, p-ethylbenzyl, 1-phenyl-1-propyl, 3-pyridinyl-1-propyl, 1-phenyl-2-sec-butyl, 4-phenyl-4-methyl-1-pentyl and the like; or with an aryl group such as phenyl, naphthyl, pyridinyl, thienyl and the like.

"Aryl" is defined as an unsaturated carbocyclic or heterocyclic moiety which may be either unsubstituted or substituted with one or more non-interfering substituent(s). Examples include, without limitation, phenyl, naphthyl, indenyl, azulenyl, fluorenyl, anthracenyl, indolyl, isoindolyl, indolinyl, benzo-furanyl, benzothiophenyl, indazolyl, benzimidazolyl, benzithiazolyl, tetrahydrofurnayl, tetrahydropyranyl, pyridyl, pyyrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbozolyl, acridinyl, phenazinyl, phenothiazinyl, phenoxazinyl and the like.

Possible substituents on an aryl group can be any non-interfering substituent. However, preferred substituents include, without limitation, alkyl, alkenyl, alkoxy, phenoxy, benzyloxy, cycloalkyl, cycloalkenyl, hydroxy, carboxy, carbonyl, amino, amido, cyano, isocyano, nitro, nitroso, nitrilo, isonitrilo, imino, azo, diazo, sulfonyl, sulfoxy, thio, thiocarbonyl, sulfhydryl, halo, haloalkyl, trifluoro-methyl, aryl and aralkyl.

$R^1$, when present, is hydrogen or lower alkyl. Examples of useful alkyl groups are shown above as possible substituents for Y.

$R^2$ is lower alkyl, aryl, aralkyl, lower alkanoyl, or —$(CH_2)_n(CHOH)_y(CH_2)_m$A wherein:

n is 1–4, preferably 1;

y is 0 or 1, preferably 0;

m is 0–5, preferably 0; and

A is cycloalkyl, cycloalkenyl, lower alkanoyl, aryl, aralkyl, —$NH_2$, —NH—(lower alkyl),

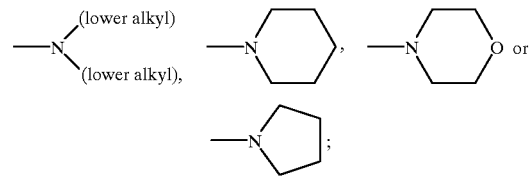

wherein "alkyl", "aryl" and "aralkyl" are as defined and/or exemplified above. Examples of useful alkanoyl groups include formyl, acetyl, propanoyl, sec-butanoyl, tert-pentanoyl (2,2-dimethylpropanoyl), benzoyl, hexanoyl, 3-methylpentanoyl, and the like.

When $R^2$ is —$(CH_2)_n(CHOH)_y(CH_2)_m$A, examples of useful groups include the following:

| n | y | m | A |
|---|---|---|---|
| 1 | 0 | 0 | cyclohexyl |
| 2 | 1 | 1 | cyclopentadienyl |
| 3 | 0 | 2 | propanoyl |
| 4 | 1 | 3 | phenyl |
| 1 | 0 | 4 | benzyl |
| 2 | 1 | 5 | —$NH_2$ |
| 3 | 0 | 1 | —N(CH$_3$)(CH$_2$CH$_3$) |
| 4 | 1 | 2 | —NHCH$_3$ |
| 1 | 0 | 3 | morpholino |

-continued

| n | y | m | A |
|---|---|---|---|
| 2 | 1 | 4 | 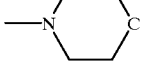 |
| 3 | 0 | 5 | 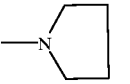 |

Preferred $R^2$ groups include methyl, ethyl, propyl, butyl and benzyl groups, with benzyl being particularly preferred.

Z in formula I can be:

| | |
|---|---|
| (i) | —$CHR^2CHR^3$—; |
| (ii) | —$R^6C$=$CR^3$—; |
| (iii) | —$R^2C$=N—; |
| (iv) | —$CR^2(OH)$—$NR^7$—; or |
| (v) | —C(O)—$NR^7$—. |

Preferably, however, Z is —$CHR^2CHR^3$—, —$R^6C$=$CR^3$— or —$R^2C$=N—.

$R^2$ and $R^3$ in formulas (i)–(v) above can be, independently, hydrogen; alkyl, such as methyl, ethyl, isopropyl, tert-butyl, n-pentyl, sec-octyl, dodecyl and the like; aryl; or aralkyl.

In formula (ii) (—$R^6C$=$CR^3$—), $R^6$ and $R^3$, independently can be hydrogen, alkyl as described above, phenyl, benzyl, chlorine, bromine, —$NO_2$, —COOH, —$COOCH_3$, or —$NR^7R^8$. When $R_3$ is —$NR^7R^8$, $R^8$ is independently hydrogen or lower alkyl as described above.

Alternatively, $R^3$ and $R^6$, taken together, can form a fused aromatic or non-aromatic, mono-, bi- or tricyclic, carbocyclic or heterocyclic ring, wherein each individual ring has 5–6 ring member atoms. Examples of such rings include a fused cyclopentadiene, pyrrole, isopyrrole, imidazole, isoimidazole, triazole, pyrazole, pyridine, thiophene, furan, thiazole, isothiazole, oxazole, isoxazole, oxadiazole, benzene, naphthalene, acridine, cyclohexane, cyclohexene, indole, pyran, pyrone, pyridine, pyrazine, pyrimidine, pyridazine, or triazine nucleus. When Z is —$R^6C$=$CR^3$— and forms a fused aromatic or non-aromatic ring, the ring formed may be substituted with one or more non-hydrogen non-interfering substituents.

Possible substituents of Y, or of the fused ring formed when Z is —$R^6C$=$CR^3$—, include any substituent that does not interfere with the reactions and purposes of the invention. Examples include, without limitation, $C_1$–$C_9$ straight or branched chain alkyl, $C_2$–$C_9$ straight or branched chain alkenyl, $C_1$–$C_9$ alkoxy, $C_2$–$C_9$, alkenyloxy, phenoxy, benzyloxy, $C_3$–$C_8$ cycloalkyl, $C_5$–$C_7$ cycloalkenyl, hydroxy, carboxy, carbonyl, amino, amido, cyano, isocyano, nitro, nitroso, nitrilo, isonitrilo, imino, azo, diazo, sulfonyl, sulfoxy, thio, thiocarbonyl, sulfhydryl, halo, haloalkyl, trifluoro-methyl, carbocyclic and heterocyclic moieties. Carbocyclic moieties include alicyclic and aromatic structures.

Preferably, however, Z is —$R^6C$=$CR^3$— where $R^6$ and $R^3$, taken together, form a fused benzene ring, and neither Y nor Z is substituted with a non-hydrogen substituent.

In the compound of the invention, the multicyclic nuclear ring structure is preferably one of the following:

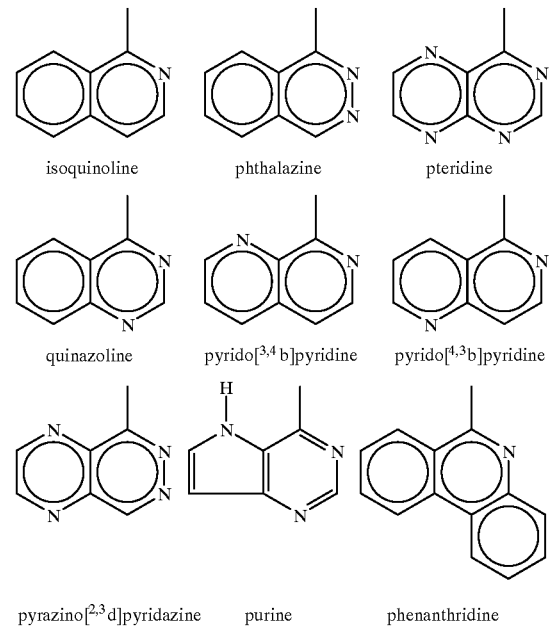

isoquinoline  phthalazine  pteridine quinazoline  pyrido[3,4 b]pyridine  pyrido[4,3 b]pyridine pyrazino[2,3 d]pyridazine  purine  phenanthridine or pharmaceutically acceptable salt, hydrate, ester, solvate, prodrug, metabolite, stereoisomer, or mixtures thereof. Preferably the compound of the invention has an isoquinoline, a phenanthridine, a phthalazine, a pteridine, or a quinazoline nucleus. More preferably it has an isoquinoline or a phthalazine nucleus.

Preferred embodiments of the invention include 1-(benzyloxy)-5-methylphthalazine (I), 1-(methoxy)-5-methylphthalazine (II), 1-(ethoxy)-5-methylphthalazine (III), 1-(propoxy)-5-methylphthalazine (IV), 1-(butoxy)-5-methylphthalazine (V), 1-(methoxy)-5-hydroxy-phthalazine (VI), 1-(ethoxy)-5-hydroxy-phthalazine (VII), 1-(propoxyoxy)-5-hydroxyphthalazine (VIII), 1-(butoxy)-5-hydroxyphthalazine (IX), 1-(benzyloxy)-5-methyl-isoquinoline (X), 1-(methoxy)-5-methylisoquinoline (XI), 1-(ethoxy)-5-methylisoquinoline (XII), 1-(propoxy)-5-methylisoquinoline (XIII), 1-(butoxy)-5-methylisoquinoline (XIV), 1-(ethoxy)-5-hydroxyisoquinoline (XV), 1-(propoxyoxy)-5-hydroxyisoquinoline (XVI) and 1-(butoxy)-5-hydroxy-isoquinoline (XVII), the structures of which follow.

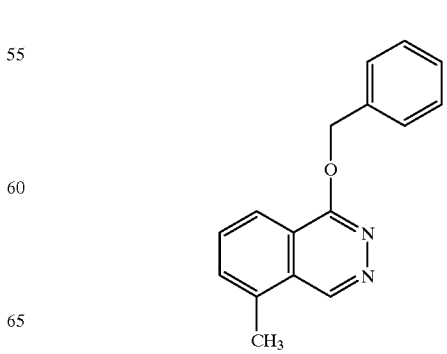

I

-continued
II
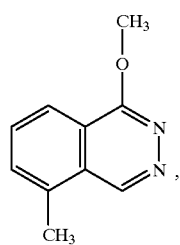
III
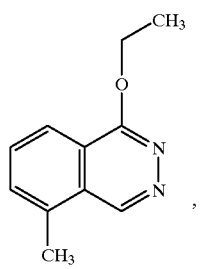
IV
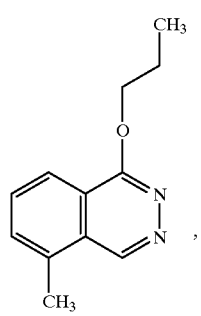
V
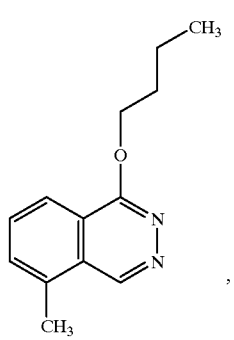
VI
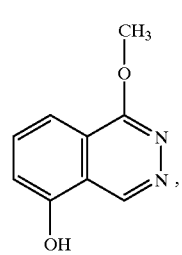
-continued
VII
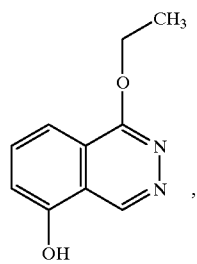
VIII
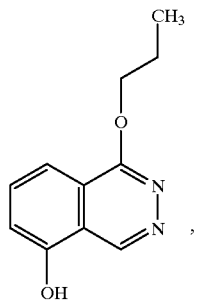
IX
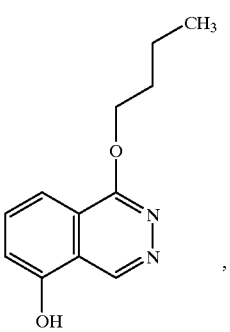
X
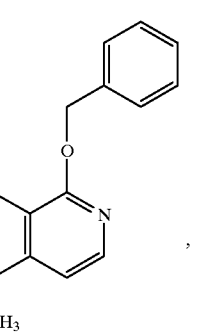
XI
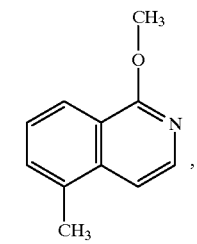

XII 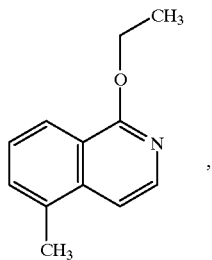,
XIII 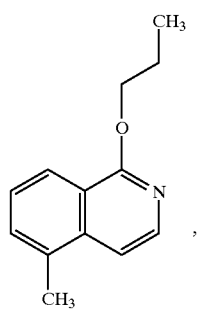,
XIV 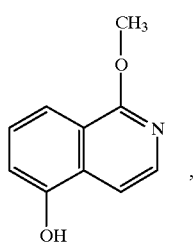,
XV 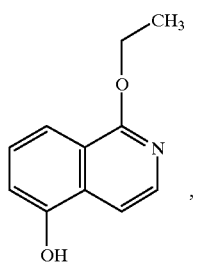,
XVI 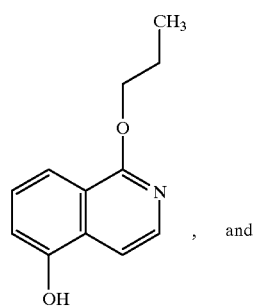, and
XVII 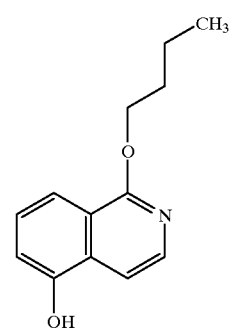.
Most preferred embodiments include 1-(benzyloxy)-5-methylphthalazine (I) and 1-(benzyloxy)-5-methyl-isoquinoline (X), which are shown above.
Additional examples of useful inhibitors are shown below in Table I:
TABLE I
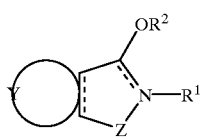
| R² | Y | Z |
|---|---|---|
| —CH₃ |  | —CH₂—CH₂— |

TABLE I-continued

| R² | Y | Z |
|---|---|---|
| —CH₂CH₃ | cyclopentene | —CH(CH₃)—CH₂— |
| —CH₂CH₂CH₃ | 2,3-dihydrofuran | —CH(C₆H₅)—CH₂— |
| —CH₂NHCH₂CH₂CH₃ | 2,3-dihydrothiophene | —CH(CH₂—C₆H₅)—CH₂— |
| —CH₂NHCH₂CH₂CH₂CH₃ | 2,3-dihydro-1H-pyrazole | —CH(CH(CH₃)₂)—CH₂— |
| —CH₂—N(CH₃)₂ | 2,3-dihydro-1H-imidazole | —C(CH₃)₂(C(CH₃)₃)—CH₂— |
| —CH₂—N(CH₂CH₃)₂ | 2,3-dihydro-1H-pyrrole | —C(C₂H₅)=CH— |
| —CH₂—N(CH₂CH₂CH₃)₂ | 2,3-dihydro-1H-1,2,3-triazole | —C(C₆H₅)=CH— |
| —CH₂N(CH₂CH₂CH₂CH₃)₂ | 2,3-dihydroisoxazole | —C(CH₂—C₆H₅)=CH— |
| —CH₂—NH₂ | cyclobutane | —CH₂—CH₂— |
| —CH₂—N(CH₃)₂ | cyclopentene | —CH(CH₃)—CH₂— |
| —CH₂N(CH₂CH₃)₂ | 2,3-dihydrofuran | —CH(C₆H₅)—CH₂— |
| CH₂CHOH—N(CH₃)₂ | thiazoline | —C(Cl)=CH— |

TABLE I-continued

| R² | Y | Z |
|---|---|---|
| CH₃−CHCHOH−N(CH₂CH₃)₂ | cyclohexadiene | −C=CH−, Br |
| −CH₂−N−CH₂Ph | cyclohexane | −C=CH−, NH−C₂H₅ |
| -sec-C₆H₁₂N(CH₃)₂ | pyran | −CH=N− |
| -tert-C₆H₁₂N(CH₃)₂ | dihydropyran | −C=N−, CH(CH₃)₂ |
| −CH₂−N(CH₂CH₃)₂ | pyridazine | −CH−NH−, OH |
| −C₂H₄−N(CH₂CH₃)₂ | pyridazine | −C(CH₃)(OH)−N(CH₃)− |
| −CH₂−cyclohexyl | pyrimidine | −CO−NH− |
| −(CH₂)₂(CHOH)CH₂−cyclopentadienyl | pyrazine | −CO−N(C₂H₅)− |
| −C(O)−CH₂CH₃ | piperazine | 3,4-dimethylthiophene |
| −(CH₂)₄(CHOH)(CH₂)₃Ph | triazine | xylene |

TABLE I-continued

| R² | Y | Z |
|---|---|---|
| —(CH₂)₆—C₆H₅ | (CH=N-CH₂-O-CH₃) | (3,4-dimethylpyridyl) |
| —(CH₂)₄—N(morpholine) | (CH₂-N(CH₃)-CH₂-O-CH₃) | —CH₂—CH₂— |
| —(CH₂)₂CHOH(CH₂)₄—N(piperidine) | (2-methyl-butadienyl) | —CH₂—CH₂— |
| —CH₂—(C₆H₅) | (cyclopentenyl) | —CH₂CH₂) |
| —(CH₂)₂-cyclopentyl | (cyclopentenyl) | —CH—CH₂—<br>CH₃ |
| —CH₂—CHOH—CH₂-cyclohexenyl | (furyl) | —CH—CH₂—<br>C₆H₅ |
| —(CH₂)₃CHOH—C(O)C₄H₉ | (thienyl) | —CH—CH₂—<br>CH₂—C₆H₅ |
| —(CH₂)₅-naphthyl | (N-NH-CH=) | —CH—CH₂—<br>CH<br>CH₃ CH₃ |
| —(CH₂)₆-pyridyl | (N=CH-NH-) | —CH—CH₂—<br>CH₃—C—CH₃<br>CH₃ |
| —(CH₂)₂CHOH(CH₂)₂-C₆H₅ | (NH-CH=CH-) | —C=CH—<br>C₂H₅ |
| —(CH₂)₄—N(morpholine) | (N=N-NH-) | —C=CH—<br>C₆H₅ |

TABLE I-continued

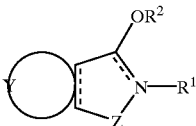

| R² | Y | Z |
|---|---|---|
| —(CH₂)₄—CHOH—(CH₂)₂—N(piperidine) | N=CH-O-CH₃ | —C(=CH—)—CH₂—C₆H₅ |
| —(CH₂)₄—N(pyrrolidine) | N=CH-S-CH₃ | —C(=CH—)—Cl |
| -tert-C₅H₁₀N(CH₃)₂ | (cyclohexenyl) | (cyclohexyl) |
| —C₆H₁₂—N(CH₃)₂ | (benzene with S-CH₃) | —C(=CH—)—NH—C₂H₅ |
| -sec-C₆H₁₂N(CH₃)₂ | (O-containing ring) | —CH=N— |
| -tert-C₆H₁₂-N(CH₃)₂ | (O-containing ring) | —C(=N—)—CH(CH₃)(CH₃) |
| —CH₂—N(CH₂CH₃)₂ | (pyridine-like N=) | —CH(OH)—NH— |
| —C₂H₄—N(CH₂CH₃)₂ | N=N (pyridazine) | —C(CH₃)(OH)—N(CH₃)(CH₃) |
| —C₃H₆—N(CH₂CH₃)₂ | N=CH-CH=N (pyrazine) | —CO—NH— |
| -sec-C₃H₆—N(CH₃)₂ | N=CH-CH=N (pyrazine) | —CO—N(C₂H₅)— |
| —C₄H₈—N(CH₃)₂ | N-CH₂-CH₂-N (piperazine) | (3,4-dimethylthiophene) |

TABLE I-continued
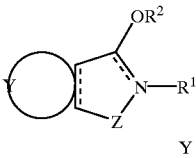
| R² | Y | Z |
|---|---|---|
| -sec-C₄H₉—N(CH₃)₂ | 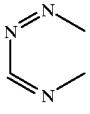 |  |
| -tert-C₄H₉—N(CH₃)₂ | 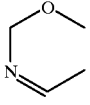 |  |
| —C₅H₁₀—N(CH₂CH₃)₂ | 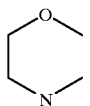 | —CH₂—CH₂— |
| —CH₂—N(CH₂CH₃)₂ | 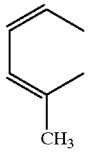 | —CH₂—CH₂— |
| —C₃H₆—N(CH₂CH₃)₂ | 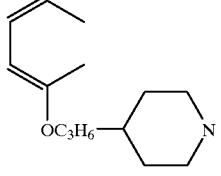 | —CH₂—CH₂— |
| —CH₃ |  | —CH₂—CH₂— |
| —CH₂(C₆H₅) |  | —CH₂—CH₂— |
|  |  | —CH₂—CH₂— |
| —C₂H₅ |  | —CH—CH₂—<br>　　CH₃ |
| —C₆H₅ |  | —CH—CH₂—<br>　　CH₃ |
|  |  | —CH—CH₂—<br>　　CH₃ |

TABLE I-continued

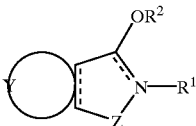

| R² | Y | Z |
|---|---|---|
| —C₃H₇ | 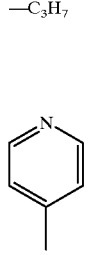 | —CH—CH₂—<br>\|<br>C₆H₅ |
|  | 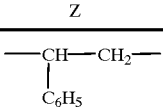 | —CH—CH₂—<br>\|<br>C₆H₅ |
| 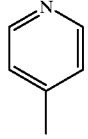 |  | —CH—CH₂—<br>\|<br>C₆H₅ |
| C₆H₁₃ | 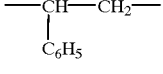 | —CH—CH₂—<br>\|<br>CH₂—C₆H₅ |
| —CH₂(C₆H₅) |  | —CH—CH₂—<br>\|<br>CH₂—C₆H₅ |
|  | 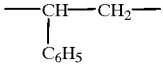 | —CH—CH₂—<br>\|<br>CH₂—C₆H₅ |
| —CH₃ |  | —CH—CH₂—<br>\|<br>CH<br>/ \\<br>CH₃ CH₃ |
| —CH₂(C₆H₅) | 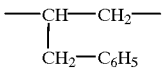 | —CH—CH₂—<br>\|<br>CH<br>/ \\<br>CH₃ CH₃ |
|  | 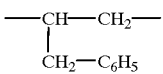 | —CH—CH₂—<br>\|<br>CH<br>/ \\<br>CH₃ CH₃ |
| —CH₃ |  | —CH—CH₂—<br>\|<br>CH₃—C—CH₃<br>\|<br>CH₃ |
| —CH₂(C₆H₅) |  | —CH—CH₂—<br>\|<br>CH₃—C—CH₃<br>\|<br>CH₃ |
| 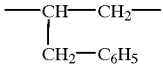 |  | —CH—CH₂—<br>\|<br>CH₃—C—CH₃<br>\|<br>CH₃ |

TABLE I-continued
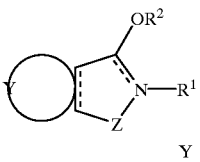
| R² | Y | Z |
|---|---|---|
| —CH₃ |  | 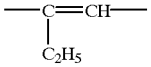 |
| —CH₂(C₆H₅) |  | 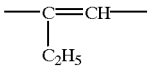 |
| —COCH₃ |  | 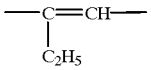 |
| —CH₃ |  | 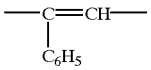 |
| —CH₂(C₆H₅) |  | 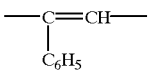 |
| —COCH₃ |  | 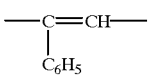 |
| —CH₃ |  | 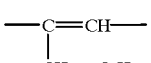 |
| —CH₂(C₆H₅) |  | 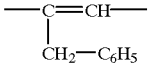 |
| —COCH₃ |  | 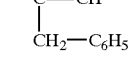 |
| —CH₃ |  | 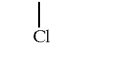 |
| —CH₂(C₆H₅) |  | 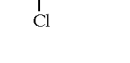 |
| —COCH₃ |  | 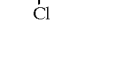 |

TABLE I-continued
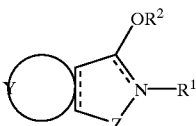
| R² | Y | Z |
|---|---|---|
| —CH₃ | 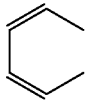 | 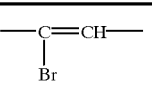 |
| —CH₂(C₆H₅) | 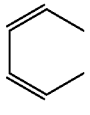 | 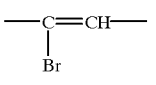 |
|  | 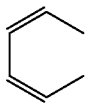 | 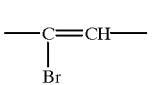 |
| —CH₃ | 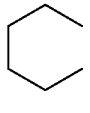 | 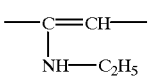 |
| —CH₂(C₆H₅) | 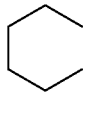 | 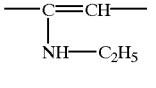 |
|  | 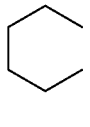 | 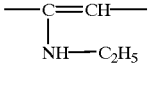 |
| —CH₃ | 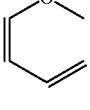 | —CH₂=N— |
| —CH₂(C₆H₅) | 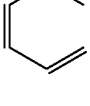 | —CH₂=N— |
|  | 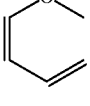 | —CH₂=N— |
| —CH₃ | 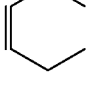 | 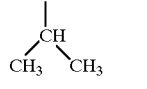 |
| —CH₂(C₆H₅) | 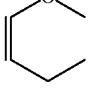 | 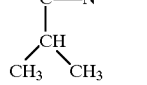 |

TABLE I-continued
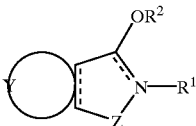
| R² | Y | Z |
|---|---|---|
| 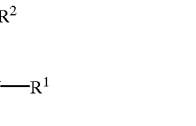 |  |  |
| —CH₃ |  |  |
| —CH₂(C₆H₅) |  | 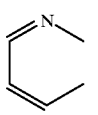 |
|  | 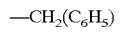 | 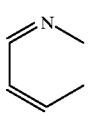 |
| —CH₃ |  |  |
| —CH₂(C₆H₅) | 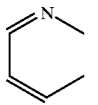 |  |
|  | 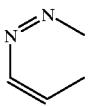 | 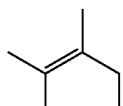 |
| —CH₃ | 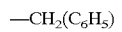 | —CO—NH— |
| —CH₂(C₆H₅) | 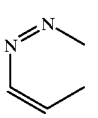 | —CO—NH— |
| 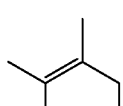 |  | —CO—NH— |

TABLE I-continued
| R² | Y | Z |
|---|---|---|
| —CH₃ | 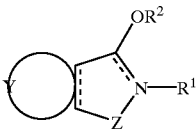 |  |
| —CH₂(C₆H₅) | 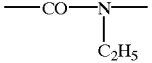 |  |
| 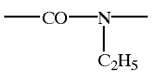 —CC₂H₅ |  | 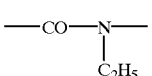 |
| —CH₃ | 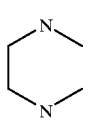 | 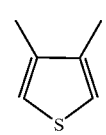 |
| —CH₂(C₆H₅) | 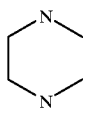 | 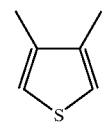 |
| 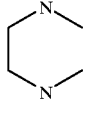 —CCH₃ | 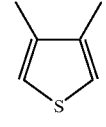 | 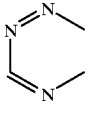 |
| —CH₃ | 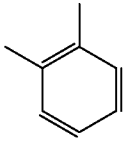 | 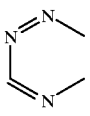 |
| —CH₂(C₆H₅) | 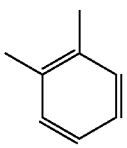 | 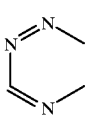 |
| 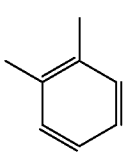 —CC₂H₅ | | |

TABLE I-continued
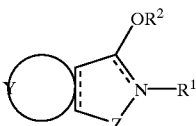
| R² | Y | Z |
|---|---|---|
| —CH₃ | 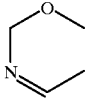 | 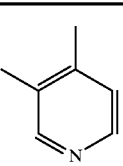 |
| —CH₂(C₆H₅) | 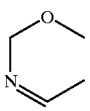 | 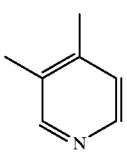 |
| $\overset{O}{\underset{\|}{-CCH_3}}$ | 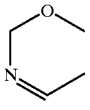 | 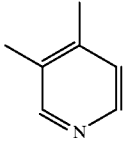 |
| —CH₃ | 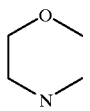 | —CH₂—CH₂— |
| —CH₂(C₆H₅) | 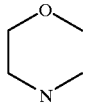 | —CH₂—CH₂— |
| $\overset{O}{\underset{\|}{-CC_2H_5}}$ | 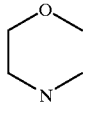 | —CH₂—CH₂— |
| —C₂H₅ | 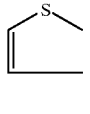 | $-\underset{CH_2-C_6H_5}{C}=CH-$ |
| —CH₃ | 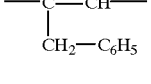 | 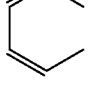 |
| —CH₂(C₆H₅) | 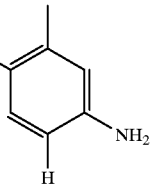 | 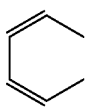 |

TABLE I-continued
| R² | Y | Z |
|---|---|---|
| 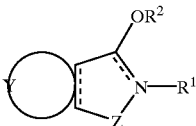 —C(O)CH₃ |  | 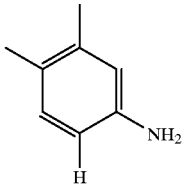 |
| —CH₃ |  | 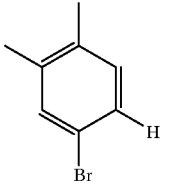 |
| —CH₂(C₆H₅) |  | 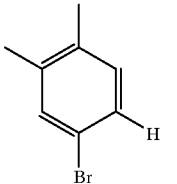 |
|  —C(O)C₂H₅ | 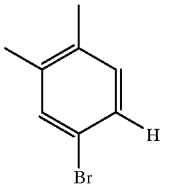 | 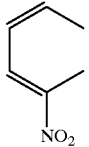 |
| —CH₃ | 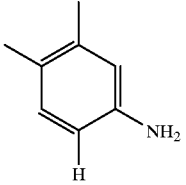 | 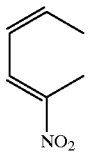 |
| —CH₂(C₆H₅) | 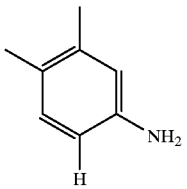 | 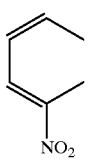 |
| 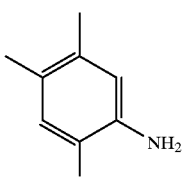 —C(O)CH₃ | | |

TABLE I-continued

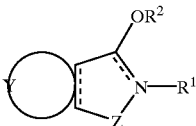

| R² | Y | Z |
|---|---|---|
| —CH₃ | 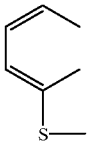 | 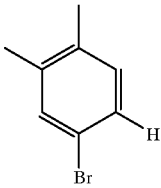 |
| —CH₂(C₆H₅) | 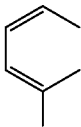 | 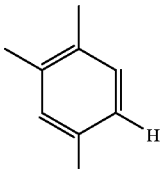 |
| $-\overset{O}{\underset{\|}{C}}C_2H_5$ |  | 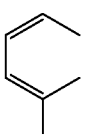 |

Also included are the pharmaceutically acceptable base or acid addition salts, hydrate, ester, solvate, prodrugs, metabolites, stereoisomers, and mixtures thereof.

The compounds of the invention may be useful in a free base form, in the form of pharmaceutically acceptable salts, pharmaceutically acceptable hydrates, pharmaceutically acceptable esters, pharmaceutically acceptable solvates, pharmaceutically acceptable prodrugs, pharmaceutically acceptable metabolites, and in the form of pharmaceutically acceptable stereoisomers. These forms are all within the scope of the invention. In practice, the use of these forms amounts to use of the neutral compound.

"Pharmaceutically acceptable salt", "hydrate", "ester" or "solvate" refers to a salt, hydrate, ester, or solvate of the inventive compounds which possesses the desired pharmacological activity and which is neither biologically nor otherwise undesirable. organic acids can be used to produce salts, hydrates, esters, or solvates such as acetate, adipate, alginate, aspartate, benzoate, benzenesulfonate, p-toluenesulfonate, bisulfate, sulfanate, sulfate, naphthylate, butyrate, citrate, camphorate, camphorsulfonate, cyclopentanepropionate, digluconate, dodecylsulfate, ethanesulfonate, fumarate, glucoheptanoate, glycerophosphate, hemisulfate heptanoate, hexanoate, 2-hydroxyethanesulfonate, lactate, maleate, methanesulfonate, 2-naphthalenesulfonate, nicotinate, oxalate, tosylate and undecanoate. Inorganic acids can be used to produce salts, hydrates, esters, or solvates such as hydrochloride, hydrobromide, hydroiodide, and thiocyanate.

Examples of suitable base salts, hydrates, esters, or solvates include hydroxides, carbonates, and bicarbonates of ammonia, alkali metal salts such as sodium, lithium and potassium salts, alkaline earth metal salts such as calcium and magnesium salts, aluminum salts, and zinc salts.

Salts, hydrates, esters, or solvates may also be formed with organic bases. organic bases suitable for the formation of pharmaceutically acceptable base addition salts, hydrates, esters, or solvates of the compounds of the present invention include those that are non-toxic and strong enough to form such salts, hydrates, esters, or solvates. For purposes of illustration, the class of such organic bases may include mono-, di-, and trialkylamines, such as methylamine, dimethylamine, triethylamine and dicyclohexylamine; mono-, di- or trihydroxyalkylamines, such as mono-, di-, and triethanolamine; amino acids, such as arginine and lysine; guanidine; N-methyl-glucosamine; N-methyl-glucamine; L-glutamine; N-methyl-piperazine; morpholine; ethylenediamine; N-benzyl-phenethylamine; (trihydroxymethyl)aminoethane; and the like. See, for example, "Pharmaceutical Salts," *J. Pharm. Sci.*, 66:1, 1–19 (1977). Accordingly, basic nitrogen-containing groups can be quaternized with agents including: lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

The acid addition salts, hydrates, esters, or solvates of the basic compounds may be prepared either by dissolving the free base of a PARP inhibitor in an aqueous or an aqueous alcohol solution or other suitable solvent containing the appropriate acid or base, and isolating the salt by evaporating the solution. Alternatively, the free base of the PARP inhibitor may be reacted with an acid, as well as reacting the PARP inhibitor having an acid group thereon with a base, such that the reactions are in an organic solvent, in which case the salt separates directly or can be obtained by concentrating the solution.

"Pharmaceutically acceptable prodrug" refers to a derivative of the inventive compounds which undergoes biotransformation prior to exhibiting its pharmacological effect(s). The prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the inventive compounds using methods known in the art, such as those described by *Burger's Medicinal Chemistry and Drug Chemistry*, Fifth Ed., Vol. 1, pp. 172–178, 949–982 (1995). For example, the inventive compounds can be transformed into prodrugs by converting one or more of the hydroxy or carboxy groups into esters.

"Pharmaceutically acceptable metabolite" refers to drugs that have undergone a metabolic transformation. After entry into the body, most drugs are substrates for chemical reactions that may change their physical properties and biologic effects. These metabolic conversions, which usually affect the polarity of the compound, alter the way in which drugs are distributed in and excreted from the body. However, in some cases, metabolism of a drug is required for therapeutic effect. For example, anticancer drugs of the antimetabolite class must be converted to their active forms after they have been transported into a cancer cell. Since must drugs undergo metabolic transformation of some kind, the biochemical reactions that play a role in drug metabolism may be numerous and diverse. The main site of drug metabolism is the liver, although other tissues may also participate.

A feature characteristic of many of these transformations is that the metabolic products, or "metabolites", are more polar than the parent drugs, although a polar drug does sometimes yield a less polar product. Substances with high lipid/water partition coefficients, which pass easily across membranes, also diffuse back readily from tubular urine through the renal tubular cells into the plasma. Thus, such substances tend to have a low renal clearance and a long persistence in the body. If a drug is metabolized to a more polar compound, one with a lower partition coefficient, its tubular reabsorption will be greatly reduced. Moreover, the specific secretory mechanisms for anions and cations in the proximal renal tubules and in the parenchymal liver cells operate upon highly polar substances.

As a specific example, phenacetin (acetophenetidin) and acetanilide are both mild analgesic and antipyretic agents, but are transformed within the body to a more polar and more effective metabolite, p-hydroxyacetanilid (acetaminophen), which is widely used today. When a dose of acetanilid is given to a person, the successive metabolites peak and decay in the plasma sequentially. During the first hour, acetanilid is the principal plasma component. In the second hour, as the acetanilid level falls, the metabolite acetaminophen concentration reaches a peak. Finally, after a few hours, the principal plasma component is a further metabolite that is inert and can be excreted from the body. Thus, the plasma concentrations of one or more metabolites, as well as the drug itself, can be pharmacologically important.

The reactions involved in drug metabolism are often classified into two groups, as shown in the Table II. Phase I are functionalization reactions, and generally consist of (1) oxidative and reductive reactions that alter and create new functional groups and (2) hydrolytic reactions that cleave esters and amides to release masked functional groups. These changes are usually in the direction of increased polarity.

Phase II reactions are conjugation reactions in which the drug, or often a metabolite of the drug, is coupled to an endogenous substrate, such as glucuronic acid, acetic acid, or sulfuric acid.

TABLE II

Phase I Reactions (functionalization reactions):

(1) Oxidation via the hepatic microsomal P450 system:
 Aliphatic oxidation
 Aromatic hydroxylation
 N-Dealkylation
 O-Dealkylation
 S-Dealkylation
 Epoxidation
 Oxidative deamination
 Sulfoxide formation
 Desulfuration
 N-Oxidation and N-hydroxylation
 Dehalogenation
(2) Oxidation via nonmicrosomal mechanisms:
 Alcohol and aldehyde oxidation
 Purine oxidation
 Oxidative deamination (monoamine oxidase and diamine oxidase)
(3) Reduction:
 Azo and nitro reduction
(4) Hydrolysis:
 Ester and amide hydrolysis
 Peptide bond hydrolysis
 Epoxide hydration Phase II Reactions (conjugation reactions):

(1) Glucuronidation
(2) Acetylation
(3) Mercapturic acid formation
(4) Sulfate conjugation
(5) N-, O-, and S-methylation
(6) Trans-sulfuration The compounds of the present invention possess one or more asymmetric center(s) and thus can be produced as mixtures (racemic and non-racemic) of stereoisomers, or as individual R- and S-stereoisomers. The individual stereoisomers may be obtained by using an optically active starting material, by resolving a racemic or non-racemic mixture of an intermediate at some appropriate stage of synthesis, or by resolving a compound of formula I.

The term "isomers" refer to compounds having the same number and kind of atoms, and hence, the same molecular weight, but differing in respect to the arrangement or configuration of the atoms. "Stereoisomers" are isomers that differ only in the arrangement of atoms in space. "Enantiomers" are a pair of stereoisomers that are non-superimposable mirror images of each other. "Diastereoisomers" are stereoisomers which are not mirror images of each other. "Racemic mixture" means a mixture containing equal, or roughly equal, parts of individual enantiomers. A "non-racemic mixture" is a mixture containing unequal, or substantially unequal, parts of individual enantiomers or stereoisomers.

Synthesis of Compounds

Many nonalkoxy-substituted PARP inhibitors can be synthesized by known methods from starting materials that are known, are themselves commercially available, or may be prepared by standard techniques of organic chemistry used to prepare corresponding compounds in the literature. See, for example, Suto et al., "Dihydroisoquinolinones: The Design and Synthesis of a New Series of Potent Inhibitors of Poly(ADP-30 ribose) Polymerase", *Anticancer Drug Des.*, 6:107–17 (1991), which discloses processes for synthesizing a number of different PARP inhibitors.

For example, the alkoxy-substituted compounds of the invention may be prepared by reacting an alkoxide with a primary alkyl halide to yield an ether by an $S_n2$ pathway, a process known as the Williamson ether synthesis. Specifically, an intermediate having formula II:

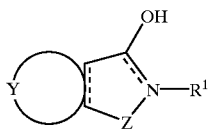

is reacted with $R^2X$, wherein X is bromo, chloro or iodo, as shown below: II

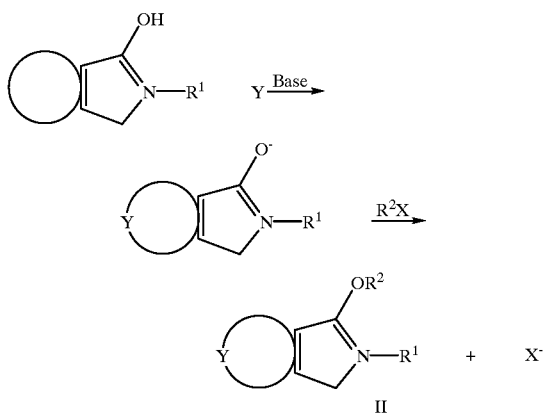

The alkoxide anion needed for the Williamson reaction to proceed is typically generated by reacting the compound of formula II with a strong base, such as sodium hydride, NaOH, KOH, $K_2CO_3$, $Na_2CO_3$, n-butyllithium or the like. The resulting acid-base reaction produces the intermediate anion for reaction with the halide $R^2X$.

More specific examples of this reaction include:

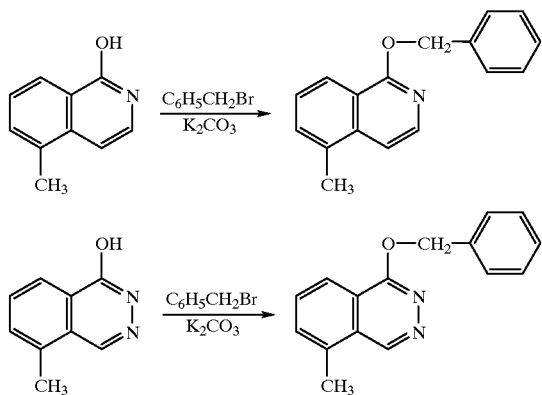

Typically, the reaction shown above takes place in a solvent that is inert with respect to both the intermediate of formula II or $R^2X$, and allows at least some of the $R^2X$ to go into solution. Typical solvents include, for example, methylene chloride, chloroform, tetrahydrofuran, dimethylformamide, and a variety of other inert organic solvents.

The above-described reaction can take place at varying temperatures depending, for example, upon the solvent used, the solubility of the intermediate of formula II and $R^2X$ in the solvent being used, and the susceptibility of the reactions to oxidize or participate in side reactions. Preferably, however, when the above reaction is used, it takes place at a temperature from about 0° C. to about 100° C., preferably at about room temperature.

The time required for the above reaction also can vary widely, depending on much the same factors. Typically, however, the reaction takes place within a time of about 5 minutes to about 24 hours, preferably from about 10 minutes to about two hours.

The addition sequence of the intermediate of formula III, the base, a solvent (if used), and the $R^2X$ compound, can vary significantly depending upon the relative reactivities of these materials, the purity of these materials, the temperature at which the reaction is performed, the degree of agitation used in the reaction, and the like. Preferably, however, the intermediate of formula II is first dissolved in a solvent, the base is first added, and the $R^2X$ compound is then added.

The product, a compound of formula I, is isolated from the reaction mixture by conventional techniques, such as by precipitating out, extraction with an immiscible solvent under appropriate pH conditions, evaporation, filtration, crystallization, or by column chromatography on silica gel and the like. Typically, however, the product is removed by either crystallization or column chromatography on silica gel.

Precursor compounds can be prepared by methods known in the art. An intermediate of formula II may be prepared by contacting an intermediate having formula III:

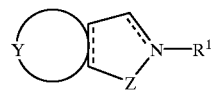

with the hydroxide of a Group I element, such as KOH or NaOH, to initiate a fusion reaction, for example, KOH fusion. The intermediate of formula III can also be prepared by other methods known in the art. See L. Paquette, *Principles of Modern Heterocyclic Chemistry*, 273–307 (1968). Other variations and modifications of this invention using the synthetic pathways described above will be obvious to those skilled in the art.

Typically, the compounds of formula I used in the composition of the invention will have an $IC_{50}$ for inhibiting poly(ADP-ribose) polymerase in vitro of 100 μM or lower, preferably 25 μM or lower, more preferably 12 μM or lower and, even more preferably, 12 mM or lower.

Pharmaceutical Compositions

A further aspect of the present invention is directed to a pharmaceutical composition comprising a pharmaceutically acceptable carrier or a diluent and a therapeutically effective amount of a compound of formula I or a pharmaceutically acceptable salt, prodrug, metabolite, stereoisomer, or mixtures (hereafter, "a compound of formula I").

The formula I compounds of the invention are useful in the manufacture of pharmaceutical formulations comprising an effective amount thereof in conjunction with or as an admixture with excipients or carriers suitable for either enteral or parenteral application. As such, formulations of the present invention suitable for oral administration may be in the form of discrete units such as capsules, cachets, tablets, troche or lozenges, each containing a predetermined amount of the active ingredient; in the form of a powder or granules; in the form of a solution or a suspension in an aqueous liquid or nonaqueous liquid; or in the form of an oil-in-water emulsion or a water-in-oil emulsion. The active ingredient may also be in the form of a bolus, electuary, or paste.

The composition will usually be formulated into a unit dosage form, such as a tablet, capsule, aqueous suspension or solution. Such formulations typically include a solid, semisolid, or liquid carrier. Exemplary carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl hydroxybenzoate, propyl hydroxybenzoate, talc, magnesium stearate, corn starch and the like.

Particularly preferred formulations include tablets and gelatin capsules comprising the active ingredient together with (a) diluents, such as lactose, dextrose, sucrose, mannitol, sorbitol, cellulose, dried corn starch, and glycine; and/or (b) lubricants, such as silica, talcum, stearic acid, its magnesium or calcium salt, and polyethylene glycol.

Tablets may also contain binders, such as magnesium aluminum silicate, starch paste, gelatin, tragacanth, methylcellulose, sodium carboxymethylcellulose and polyvinylpyrrolidone; disintegrants, such as starches, agar, alginic acid or its sodium salt, and effervescent mixtures; and/or absorbents, colorants, flavors, and sweeteners. The compositions of the invention may be sterilized and/or contain adjuvants, such as preserving, stabilizing, swelling or emulsifying agents, solution promoters, salts for regulating osmotic pressure, and/or buffers. In addition, the composition may also contain other therapeutically valuable substances. Aqueous suspensions may contain emulsifying and suspending agents combined with the active ingredient. All oral dosage forms may further contain sweetening and/or flavoring and/or coloring agents.

These compositions are prepared according to conventional mixing, granulating, or coating methods, respectively, and contain about 0.1 to 75% of the active ingredient, preferably about 1 to 50% of the same. tablet may be made by compressing or molding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent. Molded tablets may be made by molding, in a suitable machine, a mixture of the powdered active ingredient and a suitable carrier moistened with an inert liquid diluent.

When administered parenterally, the composition will normally be in a unit dosage, sterile injectable form (aqueous isotonic solution, suspension or emulsion) with a pharmaceutically acceptable carrier. Such carriers are preferably non-toxic, parenterally-acceptable and contain non-therapeutic diluents or solvents. Examples of such carriers include water; aqueous solutions, such as saline (isotonic sodium chloride solution), Ringer's solution, dextrose solution, and Hanks' solution; and nonaqueous carriers, such as 1,3-butanediol, fixed oils (e.g., corn, cottonseed, peanut, sesame oil, and synthetic mono- or di-glyceride), ethyl oleate, and isopropyl myristate.

Oleaginous suspensions can be formulated according to techniques known in the art using suitable dispersing or wetting agents and suspending agents. Among the acceptable solvents or suspending mediums are sterile fixed oils. For this purpose, any bland fixed oil may be used. Fatty acids, such as oleic acid and its glyceride derivatives, including olive oil and castor oil, especially in their polyoxyethylated forms, are also useful in the preparation of injectables. These oil solutions or suspensions may also contain long-chain alcohol diluents or dispersants.

Sterile saline is a preferred carrier, and the compounds are often sufficiently water soluble to be made up as a solution for all foreseeable needs. The carrier may contain minor amounts of additives, such as substances that enhance solubility, isotonicity, and chemical stability, e.g., antioxidants, buffers and preservatives.

When administered rectally, the composition will usually be formulated into a unit dosage form such as a suppository or cachet. These compositions can be prepared by mixing the compound with suitable non-irritating excipients that are solid at room temperature, but liquid at rectal temperature, such that they will melt in the rectum to release the compound. common excipients include cocoa butter, beeswax and polyethylene glycols or other fatty emulsions or suspensions.

Moreover, the compounds may be administered topically, especially when the conditions addressed for treatment involve areas or organs readily accessible by topical application, including neurological disorders of the eye, the skin or the lower intestinal tract.

For topical application to the eye, or ophthalmic use, the compounds can be formulated as micronized suspensions in isotonic, pH-adjusted sterile saline or, preferably, as a solution in isotonic, pH-adjusted sterile saline, either with or without a preservative such as benzylalkonium chloride. Alternatively, the compounds may be formulated into ointments, such as petrolatum.

For topical application to the skin, the compounds can be formulated into suitable ointments containing the compounds suspended or dissolved in, for example, mixtures with one or more of the following: mineral oil, liquid petrolatum, white petrolatum, propylene glycol, polyoxyethylene compound, polyoxypropylene compound, emulsifying wax and water. Alternatively, the compounds can be formulated into suitable lotions or creams containing the active compound suspended or dissolved in, for example, a mixture of one or more of the following: mineral oil, sorbitan monostearate, polysorbate 60, cetyl ester wax, cetearyl alcohol, 2-octyldodecanol, benzyl alcohol and water.

Topical application to the lower intestinal tract can be effected in rectal suppository formulations (see above) or in suitable enema formulations.

Formulations suitable for nasal or buccal administration, (such as self-propelling powder dispensing formulations), may comprise about 0.1% to about 5% w/w of the active ingredient or, for example, about 1% w/w of the same. In addition, some formulations can be compounded into a sublingual troche or lozenge.

The formulations may conveniently be presented in unit dosage form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

In a preferred embodiment, the carrier is a solid biodegradable polymer or mixture of biodegradable polymers with appropriate time release characteristics and release kinetics. The composition of the invention may then be molded into a solid implant suitable for providing efficacious concentrations of the compounds of the invention over a prolonged period of time without the need for frequent re-dosing. The composition of the present invention can be incorporated into the biodegradable polymer or polymer mixture in any suitable manner known to one of ordinary skill in the art and may form a homogeneous matrix with the biodegradable polymer, or may be encapsulated in some way within the polymer, or may be molded into a solid implant. In one embodiment, the biodegradable polymer or polymer mixture is used to form a soft "depot" containing the pharmaceutical composition of the present invention that can be administered as a flowable liquid, for example, by injection, but which remains sufficiently viscous to maintain the pharmaceutical composition within the localized area around the injection site. The degradation time of the depot so formed can be varied from several days to a few years, depending upon the polymer selected and its molecular weight. By using a polymer composition in injectable form, even the need to make an incision may be eliminated. In any event, a flexible or flowable delivery "depot" will adjust to the shape of the space it occupies within the body with a minimum of trauma to surrounding tissues. The pharmaceutical composition of the present invention is used in amounts that are therapeutically effective, and may depend upon the desired release profile, the concentration of the pharmaceutical composition required for the sensitizing effect, and the length of time that the pharmaceutical composition has to be released for treatment.

The composition of the invention is preferably administered as a capsule or tablet containing a single or divided dose of the compound, or as a sterile solution, suspension, or emulsion, for parenteral administration in a single or divided dose.

In another preferred embodiment, the compounds of the invention can be prepared in lyophilized form. In this case, 1 to 100 mg of a PARP inhibitor may be lyophilized in individual vials, together with a carrier and a buffer, such as mannitol and sodium phosphate. The composition may then be reconstituted in the vials with bacteriostatic water before administration.

The compounds of the invention are used in the composition in amounts that are therapeutically effective. While the effective amount of the PARP inhibitor will depend upon the particular compound being used, amounts of the these compounds varying from about 1% to about 65% have been easily incorporated into liquid or solid carrier delivery systems.

Compositions and Methods for Effecting Neuronal Activity

Preferably, according to the invention, an effective therapeutic amount of the compounds and compositions described above are administered to animals to effect a neuronal activity, preferably one that is not mediated by NMDA neurotoxicity. Such neuronal activity may consist of stimulation of damaged neurons, promotion of neuronal regeneration, prevention of neurodegeneration and treatment of a neurological disorder. Accordingly, the present invention further relates to a method of effecting a neuronal activity in an animal, comprising administering an effective amount of the compound of formula I to said animal. Further, the compounds of the invention inhibit PARP activity and, thus, are believed to be useful for treating neural tissue damage, particularly damage resulting from cerebral ischemia and reperfusion injury or neurodegenerative diseases in animals.

The term "nervous tissue" refers to the various components that make up the nervous system including, without limitation, neurons, neural support cells, glia, Schwann cells, vasculature contained within and supplying these structures, the central nervous system, the brain, the brain stem, the spinal cord, the junction of the central nervous system with the peripheral nervous system, the peripheral nervous system, and allied structures.

The term "ischemia" refers to localized tissue anemia due to obstruction of the inflow of arterial blood. Global ischemia occurs when blood flow to the entire brain ceases for a period of time. Global ischemia may result from cardiac arrest. Focal ischemia occurs when a portion of the brain is deprived of its normal blood supply. Focal ischemia may result from thromboembolytic occlusion of a cerebral vessel, traumatic head injury, edema or brain tumor. Even if transient, both global and focal ischemia can cause widespread neuronal damage. Although nerve tissue damage occurs over hours or even days following the onset of ischemia, some permanent nerve tissue damage may develop in the initial minutes following the cessation of blood flow to the brain. Much of this damage has been attributed to glutamate toxicity and to the secondary consequences of tissue reperfusion, such as the release of vasoactive products by damaged endothelium and the release of cytotoxic products, such as free radicals and leukotrines, by the damaged tissue. Ischemia can also occur in the heart in myocardial infarction and other cardiovascular disorders in which the coronary arteries have been obstructed as a result of atherosclerosis, thrombi, or spasm and in the eyes in retinal ischemia.

The term "neural tissue damage resulting from ischemia and reperfusion injury and neurodegenerative diseases" includes neurotoxicity, such as seen in vascular stroke and global and focal ischemia, as well as retinal ischemia.

The term "neurodegenerative diseases" includes Alzheimer's disease, Parkinson's disease and Huntington's disease.

The term "nervous insult" refers to any damage to nervous tissue and any disability or death resulting therefrom. The cause of nervous insult may be metabolic, toxic, neurotoxic, iatrogenic, thermal or chemical, and includes without limitation, ischemia, hypoxia, cerebrovascular accident, trauma, surgery, pressure, mass effect, hemmorrhage, radiation, vasospasm, neurodegenerative disease, infection, Parkinson's disease, amyotrophic lateral sclerosis (ALS), myelination/demyelination process, epilepsy, cognitive disorder, glutamate abnormality and secondary effects thereof.

The term "neuroprotective" refers to the effect of reducing, arresting or ameliorating nervous insult, and protecting, resuscitating, or reviving nervous tissue that has suffered nervous insult.

The term "preventing neurodegeneration" includes the ability to prevent neurodegeneration in patients diagnosed with a neurodegenerative disease or who are at risk of developing a neurodegenerative disease. The term also encompasses preventing further neurodegeneration in patients who are already suffering from or have symptoms of a neurodegenerative disease.

The term "treating" refers to:
(i) preventing a disease, disorder or condition from occurring in an animal that may be predisposed to the disease, disorder and/or condition, but has not yet been diagnosed as having it;
(ii) inhibiting the disease, disorder or condition, i.e., arresting its development; and
(iii) relieving the disease, disorder or condition, i.e., causing regression of the disease, disorder and/or condition.

Examples of neurological disorders that are treatable by the method of using the present invention include, without limitation, trigeminal neuralgia; glossopharyngeal neuralgia; Bell's Palsy; myasthenia gravis; muscular dystrophy; amyotrophic lateral sclerosis; progressive muscular atrophy; progressive bulbar inherited muscular atrophy; herniated, ruptured or prolapsed invertebrate disk syndromes; cervical spondylosis; plexus disorders; thoracic outlet destruction syndromes; peripheral neuropathies such as those caused by lead, dapsone, ticks, porphyria, or Guillain-Barré syndrome; Alzheimer's disease; Huntington's Disease and Parkinson's disease.

The method of the present invention is particularly useful for treating a neurological disorder selected from the group consisting of: peripheral neuropathy caused by physical injury or disease state; head trauma, such as traumatic brain injury; physical damage to the spinal cord; stroke associated with brain damage, such as vascular stroke associated with hypoxia and brain damage, focal cerebral ischemia, global cerebral ischemia, and cerebral reperfusion injury; demyelinating diseases, such as multiple sclerosis; and neurological disorders related to neurodegeneration, such as Alzheimer's Disease, Parkinson's Disease, Huntington's Disease and amyotrophic lateral sclerosis (ALS).

Treating Other PARP-Related Disorders

The compounds, compositions and methods of the present invention are particularly useful for treating or preventing tissue damage resulting from cell death or damage due to necrosis or apoptosis.

The compounds, compositions and methods of the invention can also be used to treat a cardiovascular disorder in an animal, by administering an effective amount of the compound of formula to the animal.

As used herein, the term "cardiovascular disorders" refers to those disorders that can either cause ischemia or are caused by reperfusion of the heart. Examples include, but are not limited to, coronary artery disease, angina pectoris, myocardial infarction, cardiovascular tissue damage caused by cardiac arrest, cardiovascular tissue damage caused by cardiac bypass, cardiogenic shock, and related conditions that would be known by those of ordinary skill in the art or which involve dysfunction of or tissue damage to the heart or vasculature, especially, but not limited to, tissue damage related to PARP activation.

For example, the methods of the invention are believed to be useful for treating cardiac tissue damage, particularly damage resulting from cardiac ischemia or caused by reperfusion injury in animals. The methods of the invention are particularly useful for treating cardiovascular disorders selected from the group consisting of: coronary artery disease, such as atherosclerosis; angina pectoris; myocardial infarction; myocardial ischemia and cardiac arrest; cardiac bypass; and cardiogenic shock. The methods of the invention are particularly helpful in treating the acute forms of the above cardiovascular disorders.

Further, the methods of the invention can be used to treat tissue damage resulting from cell damage or death due to necrosis or apoptosis, neural tissue damage resulting from ischemia and reperfusion injury, neurological disorders and neurodegenerative diseases; to prevent or treat vascular stroke; to treat or prevent cardiovascular disorders; to treat other conditions and/or disorders such as age-related macular degeneration, AIDS and other immune senescence diseases, arthritis, atherosclerosis, cachexia, cancer, degenerative diseases of skeletal muscle involving replicative senescence, diabetes, head trauma, immune senescence, inflammatory bowel disorders (such as colitis and Crohn's disease), muscular dystrophy, osteoarthritis, osteoporosis, chronic and/or acute pain (such as neuropathic pain), renal failure, retinal ischemia, septic shock (such as endotoxic shock), and skin aging; to extend the lifespan and proliferative capacity of cells; to alter gene expression of senescent cells; or to radiosensitize tumor cells Further still, the methods of the invention can be used to treat cancer and to radiosensitize tumor cells. The term "cancer" is interpreted broadly. The compounds of the present invention can be "anti-cancer agents", which term also encompasses "anti-tumor cell growth agents" and "anti-neoplastic agents". For example, the methods of the invention are useful for treating cancers and radiosensitizing tumor cells in cancers such as ACTH-producing tumors, acute lymphocytic leukemia, acute nonlymphocytic leukemia, cancer of the adrenal cortex, bladder cancer, brain cancer, breast cancer, cervical cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head & neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovarian cancer, ovary (germ cell) cancer, prostate cancer, pancreatic cancer, penile cancer, retinoblastoma, skin cancer, soft-tissue sarcoma, squamous cell carcinomas, stomach cancer, testicular cancer, thyroid cancer, trophoblastic neoplasms, uterine cancer, vaginal cancer, cancer of the vulva and Wilm's tumor.

The term "radiosensitizer", as used herein, is defined as molecule, preferably a low molecular weight molecule, administered to animals in therapeutically effective amounts to increase the sensitivity of the cells to be radiosensitized to electromagnetic radiation and/or to promote the treatment of diseases which are treatable with electromagnetic radiation. Diseases which are treatable with electromagnetic radiation include neoplastic diseases, benign and malignant tumors, and cancerous cells. Electromagnetic radiation treatment of other diseases not listed herein are also contemplated by the present invention. The terms "electromagnetic radiation" and "radiation" as used herein includes, but is not limited to, radiation having the wavelength of $10^{-20}$ to $10^{0}$ meters. Preferred embodiments of the present invention employ the electromagnetic radiation of: gamma-radiation ($10^{-20}$ to $10^{-13}$ m) x-ray radiation ($10^{-11}$ to $10^{-4}$ m), ultraviolet light (10 nm to 400 nm), visible light (400 nm to 700 nm), infrared radiation (700 nm to 1.0 mm), and microwave radiation (1 mm to 30 cm).

Radiosensitizers are known to increase the sensitivity of cancerous cells to the toxic effects of electromagnetic radiation. Several mechanisms for the mode of action of radiosensitizers have been suggested in the literature including: hypoxic cell radiosensitizers (e.g., 2-nitro-imidazole compounds, and benzotriazine dioxide compounds) promote the reoxygenation of hypoxic tissue and/or catalyze the generation of damaging oxygen radicals; non-hypoxic cell radiosensitizers (e.g., halogenated pyrimidines) can be analogs of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers activated by the electromagnetic radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, NPe6, tin etioporphyrin SnET2, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, to nutrients, and/or oxygen to the target cells; chemotherapeutic agents which act on the tumor with or without additional radiation; or other therapeutically effective compounds for treating cancer or other disease. Examples of additional therapeutic agents that may be used in conjunction with radiosensitizers include, but are not limited to: 5-fluorouracil, leucovorin, 5'-amino-5'deoxythymidine, oxygen, carbogen, red cell transfusions, perfluorocarbons (e.g., Fluosol-DA), 2,3-DPG, BW12C, calcium channel blockers, pentoxyfylline, antiangiogenesis compounds, hydralazine, and L-BSO. Examples of chemotherapeutic agents that may be used in conjunction with radiosensitizers include, but are not limited to: adriamycin, camptothecin, carboplatin, cisplatin, daunorubicin, docetaxel, doxorubicin, interferon (alpha, beta, gamma), interleukin 2, irinotecan, paclitaxel, topotecan, and therapeutically effective analogs and derivatives of the same.

The compounds of the present invention may also be used for radiosensitizing tumor cells.

The term "treating" refers to:
(i) preventing a disease, disorder or condition from occurring in an animal that may be predisposed to the disease, disorder and/or condition, but has not yet been diagnosed as having it;
(ii) inhibiting the disease, disorder or condition, i.e., arresting its development; and
(iii) relieving the disease, disorder or condition, i.e., causing regression of the disease, disorder and/or condition.

Administration

For medical use, the amount required of a compound of formula I to achieve a therapeutic effect will vary according to the particular compound administered, the route of administration, the animal under treatment, and the particular disorder or disease concerned. A suitable systemic dose of a compound of formula I for an animal suffering from, or likely to suffer from, any condition as described herein is typically in the range of about 0.1 to about 100 mg of base per kilogram of body weight, preferably from about 1 to about 10 mg/kg of animal body weight. It is understood that the ordinarily skilled physician or veterinarian will readily be able to determine and prescribe the amount of the compound effective for the desired prophylactic or therapeutic treatment.

In so proceeding, the physician or veterinarian may employ an intravenous bolus followed by an intravenous infusion and repeated administrations, as considered appropriate. In the methods of the present invention, the compounds may be administered, for example, orally, parenterally, by inhalation spray, topically, rectally, nasally, buccally, sublingually, vaginally, intraventricularly, or via an implanted reservoir in dosage formulations containing conventional non-toxic pharmaceutically-acceptable carriers, adjuvants and vehicles.

Parenteral includes, but is not limited to, the following examples of administration: intravenous, subcutaneous, intramuscular, intraspinal, intraosseous, intraperitoneal, intrathecal, intraventricular, intrasternal or intracranial injection and infusion techniques, such as by subdural pump. Invasive techniques are preferred, particularly direct administration to damaged neuronal tissue. While it is possible for the compound of formula I to be administered alone, it is preferable to provide it as a part of a pharmaceutical formulation.

To be effective therapeutically as central nervous system targets, the compounds used in the methods of the present invention should readily penetrate the blood-brain barrier when peripherally administered. Compounds which cannot penetrate the blood-brain barrier, however, can still be effectively administered by an intraventricular route.

The compounds used in the methods of the present invention may be administered by a single dose, multiple discrete doses or continuous infusion. Since the compounds are small, easily diffusible and relatively stable, they are well suited to continuous infusion. Pump means, particularly subcutaneous or subdural pump means, are preferred for continuous infusion.

For the methods of the present invention, any effective administration regimen regulating the timing and sequence of doses may be used. Doses of the compounds preferably include pharmaceutical dosage units comprising an efficacious quantity of active compound. By an efficacious quantity is meant a quantity sufficient to inhibit PARP activity and/or derive the desired beneficial effects therefrom through administration of one or more of the pharmaceutical dosage units. In a particularly preferred embodiment, the dose is sufficient to prevent or reduce the effects of vascular stroke or other neurodegenerative diseases.

An exemplary daily dosage unit for a vertebrate host comprises an amount of from about 0.001 mg/kg to about 50 mg/kg. Typically, dosage levels on the order of about 0.1 mg to about 10,000 mg of the active ingredient compound are useful in the treatment of the above conditions, with preferred levels being about 0.1 mg to about 1,000 mg. The specific dose level for any particular patient will vary depending upon a variety of factors, including the activity of the specific compound employed; the age, body weight, general health, sex, and diet of the patient; the time of administration; the rate of excretion; any combination of the compound with other drugs; the severity of the particular disease being treated; and the form and route of administration. Typically, in vitro dosage-effect results provide useful guidance on the proper doses for patient administration. Studies in animal models can also be helpful. The considerations for determining the proper dose levels are well-known in the art.

In methods of treating nervous insult (particularly acute ischemic stroke and global ischemia caused by drowning or head trauma), the compounds of the invention can be co-administered with one or more other therapeutic agents, preferably agents which can reduce the risk of stroke (such as aspirin) and, more preferably, agents which can reduce the risk of a second ischemic event (such as ticlopidine).

The compounds and compositions can be co-administered with one or more therapeutic agents either (i) together in a single formulation, or (ii) separately in individual formulations designed for optimal release rates of their respective active agent. Each formulation may contain from about 0.01% to about 99.99% by weight, preferably from about 3.5% to about 60% by weight, of the compound of the invention, as well as one or more pharmaceutical excipients, such as wetting, emulsifying and pH buffering agents. When the compounds used in the methods of the invention are administered in combination with one or more other therapeutic agents, specific dose levels for those agents will depend upon considerations such as those identified above for compositions and methods of the invention in general.

For example, Table III below provides known median dosages for selected chemotherapeutic agents that may be administered in combination with the compounds of the invention to such diseases or various cancers.

TABLE III

| CHEMOTHERAPEUTIC AGENT | MEDIAN DOSAGE |
|---|---|
| Asparaginase | 10,000 units |
| Bleomycin Sulfate | 15 units |
| Carboplatin | 50–450 mg |
| Carmustine | 100 mg |
| Cisplatin | 10–50 mg |
| Cladribine | 10 mg |
| Cyclophosphamide (lyophilized) | 100 mg to 2 gm |
| Cyclophosphamide (non-lyophilized) | 100 mg to 2 gm |
| Cytarabine (lyophilized powder) | 100 mg to 2 gm |
| Dacarbazine | 100–200 mg |
| Dactinomycin | 0.5 mg |
| Daunorubicin | 20 mg |
| Diethylstilbestrol | 250 mg |
| Doxorubicin | 10–150 mg |
| Etidronate | 300 mg |
| Etoposide | 100 mg |
| Floxuridine | 500 mg |
| Fludarabine Phosphate | 50 mg |
| Fluorouracil | 500 mg to 5 gm |
| Goserelin | 3.6 mg |
| Granisetron Hydrochloride | 1 mg |
| Idarubicin | 5–10 mg |
| Ifosfamide | 1–3 gm |
| Leucovorin Calcium | 50–350 mg |
| Leuprolide | 3.75–7.5 mg |
| Mechlorethamine | 10 mg |
| Medroxyprogesterone | 1 gm |
| Melphalan | 50 gm |
| Methotrexate | 20 mg to 1 gm |
| Mitomycin | 5–40 mg |
| Mitoxantrone | 20–30 mg |
| Ondansetron Hydrochloride | 40 mg |
| Paclitaxel | 30 mg |
| Pamidronate Disodium | 30–90 mg |
| Pegaspargase | 750 units |
| Plicamycin | 2,500 mcgm |
| Streptozocin | 1 gm |
| Thiotepa | 15 mg |
| Teniposide | 50 mg |
| Vinblastine | 10 mg |
| Vincristine | 1–5 mg |
| Aldesleukin | 22 million units |
| Epoetin Alfa | 2,000–10,000 units |
| Filgrastim | 300–480 mcgm |
| Immune Globulin | 500 mg to 10 gm |
| Interferon Alpha-2a | 3–36 million units |
| Interferon Alpha-2b | 3–50 million units |
| Levamisole | 50 mg |
| Octreotide | 1,000–5,000 mcgm |
| Sargramostim | 250–500 mcgm |

For the methods of the present invention, any administration regimen regulating the timing and sequence of delivery of the compound can be used and repeated as necessary to effect treatment. Such regimen may include pretreatment and/or co-administration with additional therapeutic agents.

To maximize protection of nervous tissue from nervous insult, the compounds of the invention should be administered to the affected cells as soon as possible. In situations where nervous insult is anticipated, the compounds are advantageously administered before the expected nervous insult. Such situations of increased likelihood of nervous insult include surgery, such as carotid endarterectomy, cardiac, vascular, aortic, orthopedic surgery; endovascular procedures, such as arterial catheterization (carotid, vertebral, aortic, cardia, renal, spinal, Adamkiewicz); injections of embolic agents; the use of coils or balloons for hemostasis; interruptions of vascularity for treatment of brain lesions; and predisposing medical conditions such as crescendo transient ischemic attacks, emboli and sequential strokes.

Where pre-treatment for stroke or ischemia is impossible or impracticable, it is important to bring the compounds of the invention into contact with the affected cells as soon as possible, either during or after the event. In the time period between strokes, however, diagnosis and treatment procedures should be minimized to save the cells from further damage and death. Therefore, a particularly advantageous mode of administration with a patient diagnosed with acute multiple vascular strokes is by implantation of a subdural pump to deliver the compounds of the invention directly to the infarct area of the brain. Even if comatose, it is expected that the patient would recover more quickly than he or she would without this treatment. Moreover, in any conscious state of the patient, it is expected that any residual neurological symptoms, as well as the re-occurrence of stroke, would be reduced.

As to patients diagnosed with other acute disorders believed to be related to PARP activity, such as diabetes, arthritis and Crohn's disease, the compound of the invention should also be administered as soon as possible in a single or divided dose.

Depending on the patient's presenting symptoms and the degree of response to the initial administration of the compound of the invention, the patient may further receive additional doses of the same or different compounds of the invention, by one of the following routes: parenterally, such as by injection or by intravenous administration; orally, such as by capsule or tablet; by implantation of a biocompatible, biodegradable polymeric matrix delivery system comprising the compound; or by direct administration to the infarct area by insertion of a subdural pump or a central line. It is expected that the treatment would alleviate the disorder, either in part or in its entirety and that fewer further occurrences of the disorder would develop. It also is expected that the patient would suffer fewer residual symptoms.

Where a patient is diagnosed with an acute disorder prior to the availability of the compounds of the invention, the patient's condition may deteriorate due to the acute disorder and become a chronic disorder by the time that the compounds are available. Even when a patient receives a compound of formula I for the chronic disorder, it is also expected that the patient's condition would stabilize and actually improve as a result of receiving the compound. The compounds of the present invention may also be used to prevent disorders by prophylactic administration of the compounds of the present invention.

EXAMPLES

The following examples are illustrative of preferred embodiments of the invention or related inventions and are not to be construed as limiting the present invention thereto. All polymer molecular weights are mean average molecular weights. All percentages are based on the percent by weight of the final delivery system or formulation prepared unless otherwise indicated, and all totals equal 100% by weight.

Example 1

Approximate $IC_{50}$ Data for Selected Compounds

The $IC_{50}$ of with respect to PARP inhibition was determined for several compounds by a PARP assay using purified recombinant human PARP from Trevigen (Gaithersburg, Md.), as follows: The PARP enzyme assay was set up on ice in a volume of 100 microliters consisting of 10 mM Tris-HCl (pH 8.0), 1 mM $MgCl_2$, 28 mM KCl, 28 mM NaCl, 0.1 mg/ml of herring sperm DNA (activated as a 1 mg/ml stock for 10 minutes in a 0.15% hydrogen peroxide solution), 3.0 micromolar [3H]nicotinamide adenine dinucleotide (470 mci/mmole), 7 micrograms/ml PARP enzyme, and various concentrations of the compounds to be tested. The reaction was initiated by incubating the mixture at 25° C. After 15 minutes' incubation, the reaction was terminated by adding 500 microliters of ice cold 20% (w/v) trichloroacetic acid. The precipitate formed was transferred onto a glass fiber filter (Packard Unifilter-GF/B) and washed three times with ethanol. After the filter was dried, the radioactivity was determined by scintillation counting.

Using the PARP assay described above, approximate $IC_{50}$ values were obtained for the following compounds:

| PARP Inhibitor | Approximate $IC_{50}$'s |
|---|---|
| 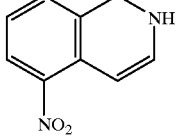 | .25 µM |
| 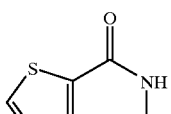 | 1.6 µM |
| 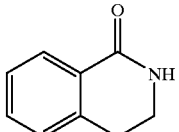 | 1.3 µM |
| 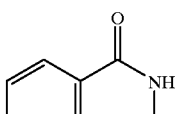 | 10 µM |

-continued

| PARP Inhibitor | Approximate $IC_{50}$'s |
|---|---|
| 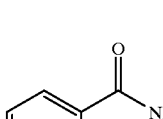 | 3.4 µM |
| | 50 µM |
| | 0.8 µM |
| | 4 µM |
| | 100 µM |
|  | 0.9 µM |

| PARP Inhibitor | Approximate IC$_{50}$'s |
|---|---|
| [structure: phenanthridinone] | 5.2 μM |
| [structure: phenanthridinone with Cl substituent] | 0.7 μM |
| [structure: phenanthridinone with F substituent] | 0.2 μM |
| [structure: phenanthridinone with Br substituent] | 1.1 μM |

Similar IC$_{50}$ values are obtained for the alkoxy-substituted compounds of the invention.

Example 2

Neuroprotective Effect of DPQ on Focal Cerebral Ischemia in Rats

Focal cerebral ischemia was produced by cauterization of the right distal MCA (middle cerebral artery) with bilateral temporary common carotid artery occlusion in male Long-Evans rats for 90 minutes. All procedures performed on the animals were approved by the University Institutional Animal Care and Use Committee of the University of Pennsylvania. A total of 42 rats (weights: 230–340 g) obtained from Charles River were used in this study. The animals fasted overnight with free access to water prior to the surgical procedure.

Two hours prior to MCA occlusion, varying amounts (control, n=14; 5 mg/kg, n=7; 10 mg/kg, n=7; 20 mg/kg, n=7; and 40 mg/kg, n=7) of the compound, 3,4-dihydro-5-[4-(1-piperidinyl)-butoxy]-1(2H)-isoquinolinone ("DPQ") were dissolved in dimethyl sulfoxide (DMSO) using a sonicator. A volume of 1.28 ml/kg of the resulting solution was injected intraperitoneally into fourteen rats.

The rats were then anesthetized with halothane (4% for induction and 0.8%–1.2% for the surgical procedure) in a mixture of 70% nitrous oxide and 30% oxygen. The body temperature was monitored by a rectal probe and maintained at 37.5±0.5° C. with a heating blanket regulated by a homeothermic blanket control unit (Harvard Apparatus Limited, Kent, U.K.). A catheter (PE-50) was placed into the tail artery, and arterial pressure was continuously monitored and recorded on a Grass polygraph recorder (Model 7D, Grass Instruments, Quincy, Mass.). Samples for blood gas analysis (arterial pH, PaO$_2$ and PaCO$_2$) were also taken from the tail artery catheter and measured with a blood gas analyzer (ABL 30, Radiometer, Copenhagen, Denmark). Arterial blood samples were obtained 30 minutes after MCA occlusion.

The head of the animal was positioned in a stereotaxic frame, and a right parietal incision between the right lateral canthus and the external auditory meatus was made. Using a dental drill constantly cooled with saline, a 3 mm burr hole was prepared over the cortex supplied by the right MCA, 4 mm lateral to the sagittal suture and 5 mm caudal to the coronal suture. The dura mater and a thin inner bone layer were kept, care being taken to position the probe over a tissue area devoid of large blood vessels. The flow probe (tip diameter of 1 mm, fiber separation of 0.25 mm) was lowered to the bottom of the cranial burr hole using a micromanipulator. The probe was held stationary by a probe holder secured to the skull with dental cement. The microvascular blood flow in the right parietal cortex was continuously monitored with a laser Doppler flowmeter (FloLab, Moor, Devon, U.K., and Periflux 4001, Perimed, Stockholm, Sweden).

Focal cerebral ischemia was produced by cauterization of the distal portion of the right MCA with bilateral temporary common carotid artery (CCA) occlusion by the procedure of Chen et al., "A Model of Focal Ischemic Stroke in the Rat: Reproducible Extensive Cortical Infarction", *Stroke* 17:738–43 (1986) and/or Liu et al., "Polyethylene Glycol-conjugated Superoxide Dismutase and Catalase Reduce Ischemic Brain Injury", *Am. J. Physiol.* 256:H589–93 (1989), both of which are hereby incorporated by reference.

Specifically, bilateral CCA's were isolated, and loops made from polyethylene (PE-10) catheter were carefully passed around the CCA's for later remote occlusion. The incision made previously for placement of the laser doppler probe was extended to allow observation of the rostral end of the zygomatic arch at the fusion point using a dental drill, and the dura mater overlying the MCA was cut. The MCA distal to its crossing with the inferior cerebral vein was lifted by a fine stainless steel hook attached to a micromanipulator and, following bilateral CCA occlusion, the MCA was cauterized with an electrocoagulator. The burr hole was covered with a small piece of Gelform, and the wound was sutured to maintain the brain temperature within the normal or near-normal range.

After 90 minutes of occlusion, the carotid loops were released, the tail arterial catheter was removed, and all of the wounds were sutured. Gentamicin sulfate (10 mg/ml) was topically applied to the wounds to prevent infection. The anesthetic was discontinued, and the animal was returned to his cage after awakening. Water and food were allowed ad libitum.

Two hours after MCA occlusion, the animals were given the same doses of the PARP inhibitor as in the pre-treatment. Twenty-four hours after MCA occlusion, the rats were sacrificed with an intraperitoneal injection of pentobarbital sodium (150 mg/kg). The brain was carefully removed from the skull and cooled in ice-cold artificial CSF for five minutes. The cooled brain was then sectioned in the coronal plane at 2 mm intervals using a rodent brain matrix (RBM-4000C, ASI Instruments, Warren, Mich.). The brain slices were incubated in phosphate-buffered saline containing 2% 2,3,5-triphenyltetrazolium chloride (TTC) at 37° C. for ten minutes. Color photographs were taken of the posterior surface of the stained slices and were used to determine the damaged area at each cross-sectional level using a computer-based image analyzer (NIH Image 1.59). To avoid artifacts due to edema, the damaged area was calculated by subtracting the area of the normal tissue in the hemisphere ipsilateral to the stroke from the area of the hemisphere contralateral to the stroke, by the method of Swanson et al., "A Semiautomated Method for Measuring Brain Infarct Volume", *J. Cereb. Blood Flow Metabol.* 10:290–93 (1990), the disclosure of which is hereby incorporated by reference. The total volume of infarction was calculated by summation of the damaged volume of the brain slices.

The cauterization of the distal portion of the right MCA with bilateral temporary CCA occlusion consistently produced a well-recognized cortical infarct in the right MCA territory of each test animal. There was an apparent uniformity in the distribution of the damaged area as measured by TTC staining in each group, as shown in FIG. 1.

In FIG. 1, the distribution of the cross-sectional infarct area at representative levels along the rostrocaudal axis was measured from the interaural line in non-treated animals and in animals treated with 10 mg/kg of 3,4-dihydro-5-[4-(1-piperidinyl)-butoxy]-1(2H)-isoquinolinone. The area of damage was expressed as mean±standard deviation. Significant differences between the 10 mg-treated group and the control group were indicated (p<0.02, p<0.01, p<0.001). The 5 mg/kg and 20 mg/kg curves fell approximately halfway between the control and the 10 mg/kg curves, whereas the 40 mg/kg curve was close to the control. The 5, 20 and 40 mg/kg curves were omitted for clarity.

PARP inhibition led to a significant decrease in the damaged volume in the 5 mg/kg-treated group (106.7±23.2 $mm^3$, p<0.001), the 10 mg/kg-treated group (76.4±16.8 $mm^3$, p<0.001), and the 20 mg/kg-treated group (110.2±42.0 $mm^3$, p<0.01), compared to the control group (165.2±34.0 $mm^3$). The data are expressed as mean±standard deviation. The significance of differences between groups was determined using an analysis of variance (ANOVA) followed by Student's t-test for individual comparisons.

There was no significant difference between the control and the 40 mg/kg-treated group (135.6±44.8 $mm^3$). However, there were significant differences between the 5 mg/kg-treated group and the 10 mg/kg-treated group (p<0.02), and between the 10 mg/kg-treated group and the 40 mg/kg-treated group (p<0.01), as shown in FIG. 2.

Figure 2:
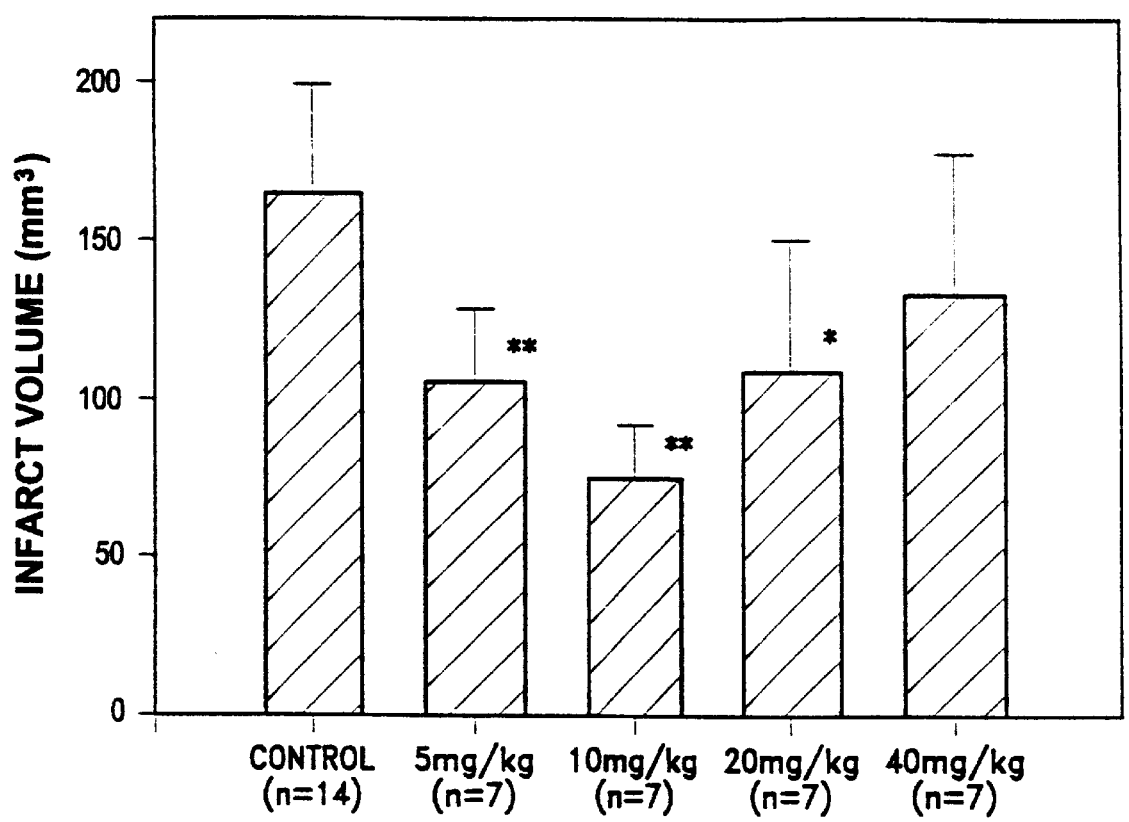
FIG. 2 shows the effect of intraperitoneal administration of 3,4-dihydro-5-[4-(1-piperidinyl)-butoxy]-1(2H)-isoquinolinone on the infarct volume.

In FIG. 2, the effect of intraperitoneal administration of 3,4-dihydro-5-[4-(1-piperidinyl)-butoxy]-1(2H)-isoaquinolinone on the infarct volume was depicted graphically. The volumes of infarct were expressed as mean±standard deviation. Significant differences between the treated groups and the control group were indicated ([+]p<0.01, [++]p<0.001). It is not clear why a high dose (40 mg/kg) of the PARP inhibitor, 3,4-dihydro-5-[4-(1-piperidinyl)-butoxy]-1(2H)-isoquinolinone, was less neuroprotective. The U-shaped dose-response curve may suggest dual effects of the compound.

However, overall, the in vivo administration of the inhibitor led to a substantial reduction in infarct volume in the focal cerebral ischemia model in the rat. This result indicated that the activation of PARP plays an important role in the pathogenesis of brain damage in cerebral ischemia.

The values of arterial blood gases ($PaO_2$, $PaCO_2$ and pH) were within the physiological range in the control and treated groups with no significant differences in these parameters among the five groups, as shown below in Table IV. A "steady state" MABP was taken following completion of the surgical preparation, just prior to occlusion; an "ischemia" MABP was taken as the average MABP during occlusion. See Table III below:

TABLE IV

|  | $PaO_2$ (mm Hg) | $PaCO_2$ (mm Hg) | pH | MABP (mm Hg) Steady State | MABP (mm Hg) Ischemia State |
|---|---|---|---|---|---|
| Control group (n = 4) | 125 ± 21 | 38.6 ± 4.6 | 7.33 ± 0.05 | 79 ± 14 | 91 ± 13[++] |
| 5 mg/kg-treated group (n = 7) | 126 ± 20 | 38.0 ± 2.8 | 7.36 ± 0.02 | 78 ± 5 | 91 ± 12[++] |
| 10 mg/kg-treated group (n = 7) | 125 ± 16 | 39.3 ± 5.2 | 7.34 ± 0.03 | 80 ± 9 | 90 ± 14[+] |
| 20 mg/kg-treated group (n = 7) | 122 ± 14 | 41.3 ± 2.8 | 7.35 ± 0.23 | 79 ± 10 | 91 ± 12[++] |
| 40 mg/kg-treated group (n = 7) | 137 ± 17 | 39.5 ± 4.7 | 7.33 ± 0.24 | 78 ± 4 | 88 ± 12[+] |

[+] = Significantly different from the steady state
[++] = Significantly different from the steady state value, p < 0.01.

There were no significant differences in any physiological parameter, including mean arterial blood pressure (MABP), prior to MCA and CCA occlusion among the five groups. Although MABP was significantly elevated following occlusion in all five groups, there were no significant differences in MABP during the occlusion period among the groups.

Since the blood flow values obtained from the laser doppler were in arbitrary units, only percent changes from the baseline (prior to occlusion) were reported. Right MCA and bilateral CCA occlusion produced a significant decrease in relative blood flow in the right parietal cortex to 20.8±7.7% of the baseline in the control group (n=5), 18.7±7.4% in the 5 mg/kg-treated group (n=7), 21.4±7.7% in the 10 mg/kg-treated group (n=7) and 19.3±11.2% in the 40 mg/kg-treated group (n=7). There were no significant differences in the blood flow response to occlusion among the four groups. In addition, blood flow showed no significant changes throughout the entire occlusion period in any group.

Following release of the carotid occlusions, a good recovery of blood flow (sometimes hyperemia) was observed in the right MCA territory of all animals. Reperfusion of the ischemic tissue resulted in the formation of NO and peroxynitrite, in addition to oxygen-derived free radicals. All of these radicals have been shown to cause DNA strand breaks and to activate PARP.

This example provided evidence that the related compounds of the present invention are effective in inhibiting PARP activity.

Example 3

Assay for Neuroprotective Effects on Focal Cerebral Ischemia in Rats

Focal cerebral ischemia experiments are performed using male Wistar rats weighing 250–300 g, which are anesthetized with 4% halothane. Anesthesia is maintained with 1.0–1.5% halothane until the end of surgery. The animals are installed in a warm environment to avoid a decrease in body temperature during surgery.

An anterior midline cervical incision is made. The right common carotid artery (CCA) is exposed and isolated from the vagus nerve. A silk suture is placed and tied around the CCA in proximity to the heart. The external carotid artery (ECA) is then exposed and ligated with a silk suture. A puncture is made in the CCA and a small catheter (PE 10, Ulrich & Co., St-Gallen, Switzerland) is gently advanced to the lumen of the internal carotid artery (ICA). The pterygopalatine artery is not occluded. The catheter is tied in place with a silk suture. Then, a 4-0 nylon suture (Braun Medical, Crissier, Switzerland) is introduced into the catheter lumen and is pushed until the tip blocks the anterior cerebral artery. The length of catheter into the ICA is approximately 19 mm from the origin of the ECA. The suture is maintained in this position by occlusion of the catheter with heat. One cm of catheter and nylon suture are left protruding so that the suture can be withdrawn to allow reperfusion. The skin incision is then closed with wound clips.

The animals are maintained in a warm environment during recovery from anesthesia. Two hours later, the animals are re-anesthetized, the clips are discarded, and the wound is re-opened. The catheter is cut, and the suture is pulled out. The catheter is then obturated again by heat, and wound clips are placed on the wound. The animals are allowed to survive for 24 hours with free access to food and water. The rats are then sacrificed with $CO_2$ and decapitated.

The brains are immediately removed, frozen on dry ice and stored at −80° C. The brains are then cut in 0.02 mm-thick sections in a cryocut at −19° C., selecting one of every 20 sections for further examination. The selected sections are stained with cresyl violet according to the Nissl procedure. Each stained section is examined under a light microscope, and the regional infarct area is determined according to the presence of cells with morphological changes.

Various doses of the compounds of the invention are tested in this model. The compounds are administered in either a single dose or a series of multiple doses, i.p. or i.v., at different times, both before or after the onset of ischemia. Compounds of the invention are found to provide protection from ischemia in the range of about 20 to 80%.

Example 4
Effects on Heart Ischemia/Reperfusion Injury in Rats

Female Sprague-Dawley rats, each weighing about 300–350 g are anesthetized with intraperitoneal ketamine at a dose of 150 mg/kg. The rats are endotracheally intubated and ventilated with oxygen-enriched room air using a Harvard rodent ventilator. Polyethylene catheters inserted into the carotid artery and the femoral vein are used for artery blood pressure monitoring and fluid administration respectively. Arterial $pCO_2$ is maintained between 35 and 45 mm Hg by adjusting the respirator rate. The rat chests are opened by median sternotomy, the pericardium is incised, and the hearts are cradled with a latex membrane tent. Hemodynamic data are obtained at baseline after at least a 15-minute stabilization period following the end of the surgical operation. The LAD (left anterior descending) coronary artery is ligated for 40 minutes, and then re-perfused for 120 minutes. After 120 minutes' reperfusion, the LAD artery is re-occluded, and a 0.1 ml bolus of monastral blue dye is injected into the left atrium to determine the ischemic risk region.

The hearts are then arrested with potassium chloride and cut into five 2–3 mm thick transverse slices. Each slice is weighed and incubated in a 1% solution of trimethyltetrazolium chloride to visualize the infarcted myocardium located within the risk region. Infarct size is calculated by summing the values for each left ventricular slice and is further expressed as a fraction of the risk region of the left ventricle.

Various doses of the compounds of the invention are tested in this model. The compounds are given either in a single dose or a series of multiple doses, i.p. or i.v., at different times, both before or after the onset of ischemia. The compounds of the invention are found to have ischemia/reperfusion injury protection in the range of 10 to 40 percent. Therefore, they protect against ischemia-induced degeneration of rat hippocampal neurons in vitro.

Example 5
Retinal Ischemia Protection

A patient just diagnosed with acute retinal ischemia is immediately administered parenterally, either by intermittent or continuous intravenous administration, a compound of Formula I, either as a single dose or a series of divided doses of the compound. After this initial treatment, and depending on the patient's presenting neurological symptoms, the patient optionally may receive the same or a different compound of the invention in the form of another parenteral dose. It is expected by the inventors that significant prevention of neural tissue damage would ensue and that the patient's neurological symptoms would considerably lessen due to the administration of the compound, leaving fewer residual neurological effects post-stroke. In addition, it is expected that the re-occurrence of retinal ischemia would be prevented or reduced.

Example 6
Treatment of Retinal Ischemia

A patient has just been diagnosed with acute retinal ischemia. Immediately, a physician or a nurse parenterally administers a compound of Formula I, either as a single dose or as a series of divided doses. The patient also receives the same or a different PARP inhibitor by intermittent or continuous administration via implantation of a biocompatible, biodegradable polymeric matrix delivery system comprising a compound of Formula I, or via a subdural pump inserted to administer the compound directly to the infarct area of the brain. It is expected by the inventors that the patient would awaken from the coma more quickly than if the compound of the invention were not administered. The treatment is also expected to reduce the severity of the patient's residual neurological symptoms. In addition, it is expected that re-occurrence of retinal ischemia would be reduced.

Example 7
Vascular Stroke Protection

A patient just diagnosed with acute vascular stroke is immediately administered parenterally, either by intermittent or continuous intravenous administration, a compound of Formula I, either as a single dose or a series of divided doses of the compound. After this initial treatment, and depending on the patient's presenting neurological symptoms, the patient optionally may receive the same or a different compound of the invention in the form of another parenteral dose. It is expected by the inventors that significant prevention of neural tissue damage would ensue and that the patient's neurological symptoms would considerably lessen due to the administration of the compound, leaving fewer residual neurological effects post-stroke. In addition, it is expected that the re-occurrence of vascular stroke would be prevented or reduced.

Example 8
Treatment of Vascular Stroke

A patient has just been diagnosed with acute multiple vascular strokes and is comatose. Immediately, a physician or a nurse parenterally administers a compound of Formula I, either as a single dose or as a series of divided doses. Due to the comatose state of the patient, the patient also receives the same or a different PARP inhibitor by intermittent or continuous administration via implantation of a biocompatible, biodegradable polymeric matrix delivery system comprising a compound of Formula I, or via a subdural pump inserted to administer the compound directly to the infarct area of the brain. It is expected by the inventors that the patient would awaken from the coma more quickly than if the compound of the invention were not administered. The treatment is also expected to reduce the severity of the patient's residual neurological symptoms. In addition, it is expected that re-occurrence of vascular stroke would be reduced.

Example 9
Preventing Cardiac Reperfusion Injury

A patient is diagnosed with life-threatening cardiomyopathy and requires a heart transplant. Until a donor heart is found, the patient is maintained on Extra Corporeal Oxygenation Monitoring (ECMO).

A donor heart is then located, and the patient undergoes a surgical transplant procedure, during which the patient is placed on a heart-lung pump. The patient receives a compound of the invention intracardiac within a specified period of time prior to re-routing his or her circulation from the heart-lung pump to his or her new heart, thus preventing cardiac reperfusion injury as the new heart begins to beat independently of the external heart-lung pump.

Example 10
Septic Shock Assay

Groups of 10 C57/BL male mice weighing 18 to 20 g were administered a test compound, 1-carboxynaphthalene-1-carboxamide at the doses of 60, 20, 6 and 2 mg/kg, daily, by intraperitoneal (IP) injection for three consecutive days. Each animal was first challenged with lipopolysaccharide (LPS, from $E.$ $Coli$, $LD_{100}$ of 20 mg/animal IV) plus galactosamine (20 mg/animal IV). The first dose of test compound in a suitable vehicle was given 30 minutes after challenge, and the second and third doses were given 24 hours later on day 2 and day 3 respectively, with only the surviving animals receiving the second or third dose of the test compound. Mortality was recorded every 12 hours after challenge for the three-day testing period. 1-Carboxynaphthalene-1-carboxamide provided a protection against mortality from septic shock of about 40%. Based on these results, other compounds of the invention are expected to provide a protection against mortality exceeding about 35%.

Example 11
In vitro Radiosensitization

The human prostate cancer cell line, PC-3s, were plated in 6 well dishes and grown at monolayer cultures in RPMI1640 supplemented with 10% FCS. The cells are maintained at 37° C. in 5% $CO_2$ and 95% air. The cells were exposed to a dose response (0.1 mM to 0.1 $\mu$M) of 3 different PARP inhibitors of Formula I disclosed herein prior to irradiation at one sublethal dose level. For all treatment groups, the six well plates were exposed at room temperature in a Seifert 250 kV/15 mA irradiator with a 0.5 mm Cu/l mm. Cell viability was examined by exclusion of 0.4% trypan blue. Dye exclusion was assessed visually by microscopy and viable cell number was calculated by subtracting the number of cells from the viable cell number and dividing by the total number of cells. Cell proliferation rates were calculated by the amount of $^3$H-thymidine incorporation post-irradiation. The PARP inhibitors show radiosensitization of the cells.

Example 12
In vivo Radiosensitization

Before undergoing radiation therapy to treat cancer, a patient is administered an effective amount of a compound or a pharmaceutical composition of the present invention. The compound or pharmaceutical composition acts as a radiosensitizer and making the tumor more susceptible to radiation therapy.

Example 13
Measuring Altered Gene Expression in mRNA Senescent Cells

Human fibroblast BJ cells, at Population Doubling (PDL) 94, are plated in regular growth medium and then changed to low serum medium to reflect physiological conditions described in Linskens, et al., $Nucleic$ $Acids$ $Res.$ 23:16:3244–3251 (1995). A medium of DMEM/199 wupplemented with 0.5% bovine calf serum is used. The cells are treated daily for 13 days with the PARP inhibitor of Formula I as disclosed herein. The control cells are treated with and without the solvent used to administer the PARP inhibitor. The untreated old and young control cells are tested for comparison. RNA is prepared from the treated and control cells according to the techniques described in PCT Publication No. 96/13610 and Northern blotting is conducted. Probes specific for senescence-related genes are analyzed, and treated and control cells compared. In analyzing the results, the lowest level of gene expression is arbitrarily set at 1 to provide a basis for comparison. Three genes particularly relevant to age-related changes in the skin are collagen, collagenase and elastin. West, $Arch.$ $Derm.$ 130:87–95 (1994). Elastin expression of the cells treated with the PARP inhibitor of Formula I is significantly increased in comparison with the control cells. Elastin expression is significantly higher in young cells compared to senescent cells, and thus treatment with the PARP inhibitor of Formula I causes elastin expression levels in senescent cells to change to levels similar to those found in much younger cells. Similarly, a beneficial effect is seen in collagenase and collagen expression with treatment with the PARP inhibitors of Formula I.

Example 14
Measuring Altered Gene Expression Protein in Senescent Cells

Approximately 105 BJ cells, at PDL 95–100 are plated and grown in 15 cm dishes. The growth medium is DMEM/199 supplemented with 10% bovice calf serum. The cells are treated daily for 24 hours with the PARP inhibitors of Formula I (100 $\mu$g/1 mL of medium). The cells are washed with phosphate buffered solution (PBS), then permeablized with 4% paraformaldehyde for 5 minutes, then washed with PBS, and treated with 100% cold methanol for 10 minutes. The methanol is removed and the cells are washed with PBS, and then treated with 10% serum to block nonspecific antibody binding. About 1 mL of the appropriate commercially available antibody solutions (1:500 dilution. Vector) is added to the cells and the mixture incubated for 1 hour. The cells are rinsed and washed three times with PBS. A secondary antibody, goat anti-mouse IgG (1 mL) with a biotin tag is added along with 1 mL of a solution containing streptavidin conjugated to alkaline phosphatase and 1 mL of NBT reagent (Vector). The cells are washed and changes in gene expression are noted calorimetrically. Four senescence-specific genes—collagen I, collagen III, collagenase, and interferon gamma—in senescent cells treated with the PARP inhibitor of Formula I are monitored and the results show a decrease in interferon gamma expression with no observable change in the expression levels of the other three genes, demonstrating that the PARP inhibitors of Formula I can alter senescence-specific gene expression.

Example 15
Extending or Increasing Proliferative Capacity and Lifespan of Cells

To demonstrate the effectiveness of the present method for extending the proliferative capacity and lifespan of cells, human fibroblast cells lines (either W138 at Population Doubling (PDL) 23 or BJ cells at PDL 71) are thawed and plated on T75 flasks and allowed to grow in normal medium (DMEM/M199 plus 10% bovine calf serum) for about a week, at which time the cells are confluent, and the cultures are therefor ready to be subdivided. At the time of subdivision, the media is aspirated, and the cells rinsed with phosphate buffer saline (PBS) and then trypsinized. The cells are counted with a Coulter counter and plated at a density of $10^5$ cells per $cm^2$ in 6-well tissue culture plates in DMEM/199 medium supplemented with 10% bovine calf serum and varying amounts (0.10 $\mu$M, and 1 mM: from a 100×stock solution in DMEM/M199 medium) of a PARP inhibitor of Formula I as disclosed herein. This process is repeated every 7 days until the cell appear to stop dividing. The untreated (control) cells reach senescence and stop dividing after about 40 days in culture. Treatment of cells with 10 $\mu$M 3-AB appears to have little or no effect in contrast to treatment with 100 $\mu$M 3-AB which appears lengthen the lifespan of the cells and treatment with 1 mM 3-AB which dramatically increases the lifespan and proliferative capacity of the cells. The cells treated with 1 mM 3-AB will still divide after 60 days in culture.

Example 16
Neuroprotective Effects of Formula I on Chronic Constriction Injury (CCI) in Rats Adult male Sprague-Dawley rats, 300–350 g, are anesthetized with intraperitoneal 50 mg/kg sodium pentobarbital. Nerve ligation is performed by exposing one side of the rat's sciatic nerves and dissecting a 5–7 mm-long nerve segment and closing with four loose ligatures at a 1.0–1.5-mm, followed by implanting of an intrathecal catheter and inserting of a gentamicin sulfate-flushed polyethylene (PE-10) tube into the subarachnoid space through an incision at the cisterna magna. The caudal end of the catheter is gently threaded to the lumbar enlargement and the rostral end is secured with dental cement to a screw embedded in the skull and the skin wound is closed with wound clips.

Thermal hyperalgesia to radiant heat is assessed by using a paw-withdrawal test. The rat is placed in a plastic cylinder on a 3-mm thick glass plate with a radiant heat source from a projection bulb placed directly under the plantar surface of the rat's hindpaw. The paw-withdrawal latency is defined as the time elapsed from the onset of radiant heat stimulation to withdrawal of the rat's hindpaw.

Mechanical hyperalgesia is assessed by placing the rat in a cage with a bottom made of perforated metal sheet with many small square holes. Duration of paw-withdrawal is recorded after pricking the mid-plantar surface of the rat's hindpaw with the tip of a safety pin inserted through the cage bottom.

Mechano-allodynia is assessed by placing a rat in a cage similar to the previous test, and applying von Frey filaments in ascending order of bending force ranging from 0.07 to 76 g to the mid-plantar surface of the rat's hindpaw. A von Frey filament is applied perpendicular to the skin and depressed slowly until it bends. A threshold force of response is defined as the first filament in the series to evoke at least one clear paw-withdrawal out of five applications.

Dark neurons are observed bilaterally within the spinal cord dorsal horn, particularly in laminae I–II, of rats 8 days after unilateral sciatic nerve ligation as compared with sham operated rats. Various doses of differing compounds of Formula I are tested in this model and show that the Formula I compounds reduce both incidence of dark neurons and neuropathic pain behavior in CCI rats.

The invention being thus described, it will be obvious that the same may be varied in many ways. Such variations are not to be regarded as a departure from the spirit and scope of the invention, and all such modifications are intended to be included within the scope of the following claims.

We claim:

1. A method of treating a cardiovascular disorder in an animal comprising administering to said animal an effective amount of a compound of formula I:

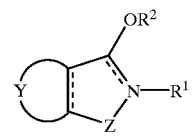

or a pharmaceutically acceptable salt, hydrate, ester, solvate, prodrug, metabolite, stereoisomer, or mixtures thereof, wherein:

$R^1$, when present, is hydrogen or lower alkyl;

$R^2$ is lower alkyl, aryl, aralkyl, lower alkanoyl, or —(CH$_2$)$_n$—(CHOH)$_y$(CH$_2$)$_m$A, wherein n is 1–4, y is 0 or 1, m is 0–5, and A is cycloalkyl, cycloalkenyl, lower alkanoyl, aryl, aralkyl, —NH$_2$, —NH—(lower alkyl),

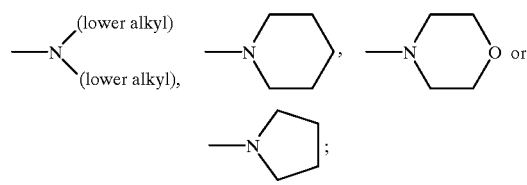

Y represents the atoms necessary to form a fused 5- to 6-membered ring that is aromatic or nonaromatic and carbocyclic, which may be substituted or unsubstituted;

Z is (i) —CHR$^2$CHR$^3$— where $R^2$ and $R^3$ are independently hydrogen, alkyl, aryl or aralkyl; or (ii) —R$^6$C═CR$^3$— where $R^6$ and $R^3$ are independently hydrogen, lower alkyl, aryl, aralkyl, chlorine, bromine or —NR$^7$R$^8$, where $R^7$ and $R^8$ are independently hydrogen or lower alkyl, or, $R^6$ and $R^3$, taken together, form a fused 5- to 6-membered ring that is aromatic or nonaromatic and carbocyclic or heterocyclic.

2. The method of claim 1, wherein the cardiovascular disorder is coronary artery disease, myocardial infarction, angina pectoris, cardiogenic shock or cardiovascular tissue damage.

3. The method of claim 1 wherein Y is a 6 membered aromatic carbocyclic ring.

4. The method of claim 3 wherein Y contains at least one substitueut.

5. The method of claim 4 wherein said at least one substitueut is selected from the group consisting of an alkyl group, an alkenyl group, an alkynyl group, an alkanoyl group, a cycloalkyl group, a cycloalkenyl group, an arakyl group and an aryl group.

6. The method of claim 5 wherein $R^2$ is —$(CH_2)_n$—$(CHOH)_y$—$(CH_2)_m$A.

7. The method of claim 6 wherein A is aralkyl.

8. The method of claim 7 wherein said compound is 1-(benzyloxy)-5-methylisoquinoline.

9. The method of claim 1 wherein said compound is selected from the group consisting of 1-(methoxy-)-5-methylisoquinoline, 1-(ethoxy-)-5-methylisoquinoline, 1-(propoxy)-5-methylisoquinoline, 1-(butoxy)-5-methylisoquinoline, 1-(ethoxy)-5-hydroxyisoquinoline, 1-(propoxy)-5-hydroxyisoquinoline and 1-(butoxy)-5-hydroxyisoquinoline.

10. The method of claim 3, wherein the cardiovascular disorder is coronary artery disease, myocardial infarction, angina pectoris, cardiogenic shock or cardiovascular tissue damage.

11. The method of claim 4, wherein the cardiovascular disorder is coronary artery disease, myocardial infarction, angina pectoris, cardiogenic shock or cardiovascular tissue damage.

12. The method of claim 5, wherein the cardiovascular disorder is coronary artery disease, myocardial infarction, angina pectoris, cardiogenic shock or cardiovascular tissue damage.

13. The method of claim 6, wherein the cardiovascular disorder is coronary artery disease, myocardial infarction, angina pectoris, cardiogenic shock or cardiovascular tissue damage.

14. The method of claim 7, wherein the cardiovascular disorder is coronary artery disease, myocardial infarction, angina pectoris, cardiogenic shock or cardiovascular tissue damage.

15. The method of claim 8, wherein the cardiovascular disorder is coronary artery disease, myocardial infarction, angina pectoris, cardiogenic shock or cardiovascular tissue damage.

16. The method of claim 9, wherein the cardiovascular disorder is coronary artery disease, myocardial infarction, angina pectoris, cardiogenic shock or cardiovascular tissue damage.

17. The method of claim 1 wherein said compound has an $IC_{50}$ of 100 μm or lower for inhibiting poly (ADP-ribose) polymerase in vitro.

18. The method of claim 3 wherein A is cycloalkyl, cycloalkenyl, lower alkanoyl, aryl, aralkyl,

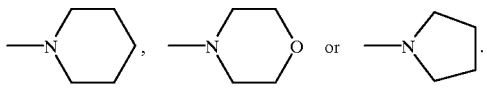

19. The method of claim 4 wherein A is cycloakyl, cycloalkonyl, lower alkanoyl, aryl, aralkyl,

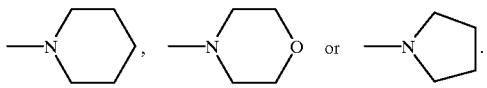

20. The method of claim 5 wherein A is cycloalkyl, cycloalkenyl, lower alkanoyl, aryl, aralkyl,

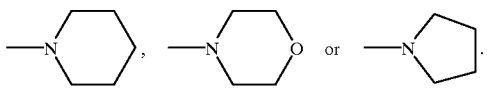

21. The method of claim 6 wherein A is cycloalkyl, cycloalkenyl, lower alkanoyl, aryl, aralkyl,

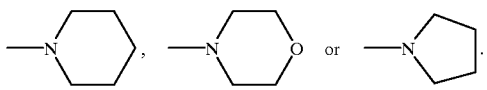

22. The method of claim 18 wherein the cardiovascular disorder is coronary artery disease, myocardial infraction, angina pectoris, cardiogenic shock or cardiovascular tissue damage.

23. The method of claim 18 wherein said compound has an $IC_{50}$ of 100 μm or lower for inhibiting poly (ADP-ribose) polymerase in vitro.

* * * * *